(12) United States Patent
Subramaniam et al.

(10) Patent No.: US 9,844,347 B2
(45) Date of Patent: Dec. 19, 2017

(54) ELECTROMAGNETIC SYSTEM AND METHOD

(71) Applicant: The Ohio State University, Columbus, OH (US)

(72) Inventors: Vishwanath Subramaniam, Westerville, OH (US); Joseph West, Richwood, OH (US); Jennifer McFerran Brock, Anchorage, AK (US); Emily Sequin, Columbus, OH (US); Duxin Sun, Ann Arbor, MI (US); Peng Zou, Columbus, OH (US); Travis Hamilton Jones, Columbus, OH (US)

(*) Notice: Subject to any disclaimer, the term of this patent is extended or adjusted under 35 U.S.C. 154(b) by 913 days.

(21) Appl. No.: 14/257,200

(22) Filed: Apr. 21, 2014

(65) Prior Publication Data

US 2014/0228671 A1    Aug. 14, 2014

Related U.S. Application Data

(63) Continuation-in-part of application No. 13/210,293, filed on Aug. 15, 2011, now abandoned, which is a
(Continued)

(51) Int. Cl.
*A61B 5/00* (2006.01)
*A61B 5/05* (2006.01)
*G01N 27/02* (2006.01)

(52) U.S. Cl.
CPC .............. *A61B 5/7282* (2013.01); *A61B 5/05* (2013.01); *A61B 5/415* (2013.01); *A61B 5/418* (2013.01); *G01N 27/025* (2013.01)

(58) Field of Classification Search
CPC ......... A61B 5/7282; A61B 5/05; A61B 5/415; A61B 5/418; G01N 27/025
See application file for complete search history.

(56) References Cited

U.S. PATENT DOCUMENTS

| 4,250,451 A | 2/1981 | Slagle |
| 4,690,149 A | 9/1987 | Ko |

(Continued)

FOREIGN PATENT DOCUMENTS

| WO | 2002076294 A2 | 10/2002 |
| WO | 2005057467 A2 | 6/2005 |
| WO | 2006/135520 | * 12/2006 |

OTHER PUBLICATIONS

Gencer et al., Imaging Tissue Conductivity via Contactless Measurements: A Feasibility Study. Elektrik, vol. 6, No. 3, 1998.
(Continued)

*Primary Examiner* — Amanda Lauritzen Moher
(74) *Attorney, Agent, or Firm* — Standley Law Group LLP

(57) ABSTRACT

Differences of electromagnetic (EM) properties between healthy and cancerous tissues allow detection of abnormal conditions occurring in a tissue of an animal, for example, intra-operative cancer detection. By using a time-varying EM field, electrical eddy currents are generated in the tissue sample, and assessed using phase-sensitive detection. In some aspects, a change in phase shift between the voltage in a receiver coil and the voltage in a driver coil provide a direct and immediate indication of differences in EM properties of specimens.

14 Claims, 24 Drawing Sheets

Related U.S. Application Data continuation of application No. PCT/US2010/000444, filed on Feb. 16, 2010.

(60) Provisional application No. 61/152,408, filed on Feb. 13, 2009, provisional application No. 61/234,745, filed on Aug. 18, 2009, provisional application No. 61/239,652, filed on Sep. 3, 2009.

(56) References Cited

U.S. PATENT DOCUMENTS

| | | | |
|---|---|---|---|
| 5,390,673 | A | 2/1995 | Kikinis |
| 5,514,337 | A | 5/1996 | Groger et al. |
| 5,810,742 | A | 9/1998 | Pearlman |
| 6,418,335 | B2 | 7/2002 | Avrin et al. |
| 6,813,515 | B2 | 11/2004 | Hashimshony |
| 6,876,878 | B2 | 4/2005 | Zhdanov |
| 7,283,868 | B2 | 10/2007 | Ko et al. |
| 7,505,811 | B2 | 3/2009 | Hashimshony |
| 7,865,236 | B2 * | 1/2011 | Cory .................. A61B 5/0536 600/547 |
| 2003/0016010 | A1 | 1/2003 | Kandori et al. |
| 2003/0055358 | A1 | 3/2003 | Ko et al. |
| 2005/0090732 | A1 | 4/2005 | Ivkov et al. |
| 2006/0293597 | A1 | 12/2006 | Johnson et al. |
| 2008/0021343 | A1 * | 1/2008 | Hashimshony ........ A61B 5/053 600/547 |
| 2008/0204009 | A1 * | 8/2008 | Gleich .................. A61B 5/05 324/228 |
| 2008/0224688 | A1 | 9/2008 | Rubinsky et al. |
| 2008/0234574 | A1 | 9/2008 | Hancock et al. |
| 2008/0246472 | A1 | 10/2008 | Igney et al. |
| 2011/0034974 | A1 | 2/2011 | Munoz Marquez et al. |

OTHER PUBLICATIONS

Korjenevsky et al., Magnetic induction tomography: experimental realization, 2000, IOP Publishing Ltd.

Richer et al., Eddy Current Based Flexible Sensor for Contactless Measurement of Breathing, Instrumentation and Measurement Technology Conference, Ottawa, Canada, May 17-19, 2005.

Ambia et al., Electrical Impedance Imaging Using Eddy Current, Proceedings of World Academy of Science, Engineering and Technology, vol. 30, Jul. 30, 2008.

Wansapura et al., Temperature Mapping of Frozen Tissue Using Eddy Current Compensated Half Excitation Rf Pulses, Magnetic Resonance in Medicine, pp. 985-992, 2001.

Sharma, et al., Transmission of Time Varying Magnetic Field Through Body Tissue, Journal Biological Physics, vol. 3, pp. 95-102, 1975.

* cited by examiner

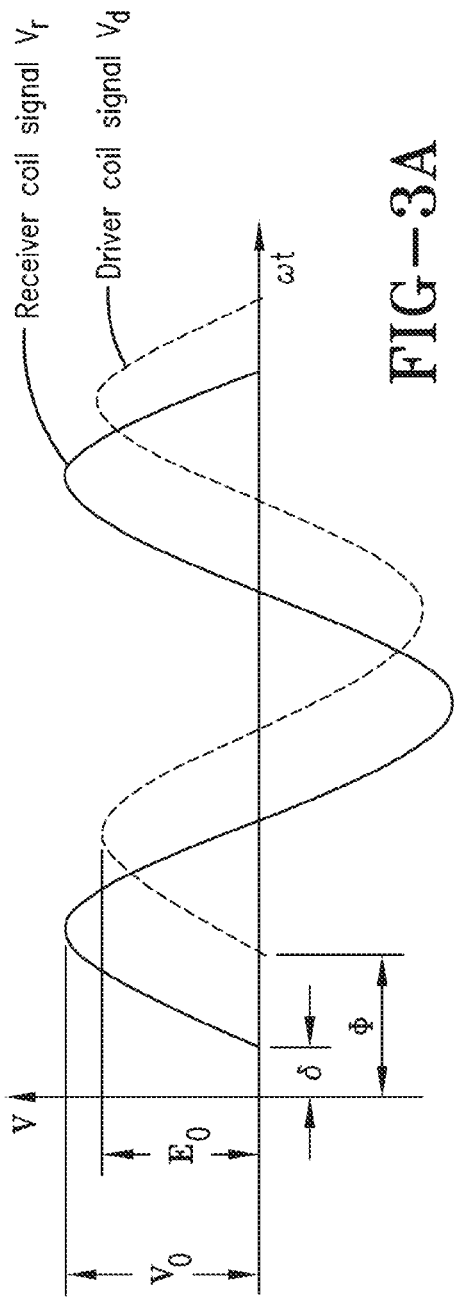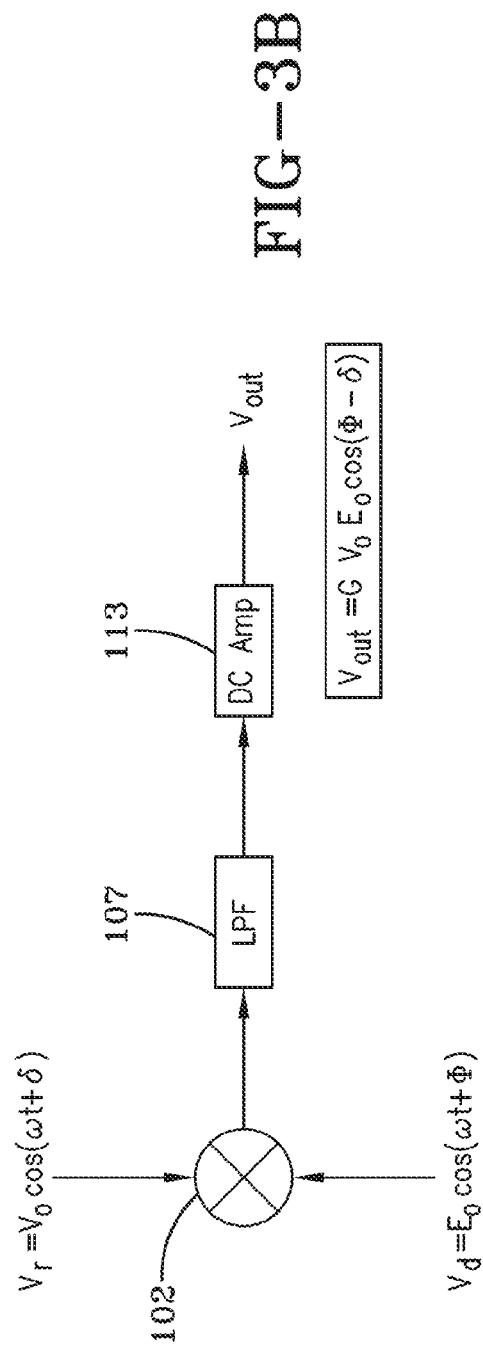

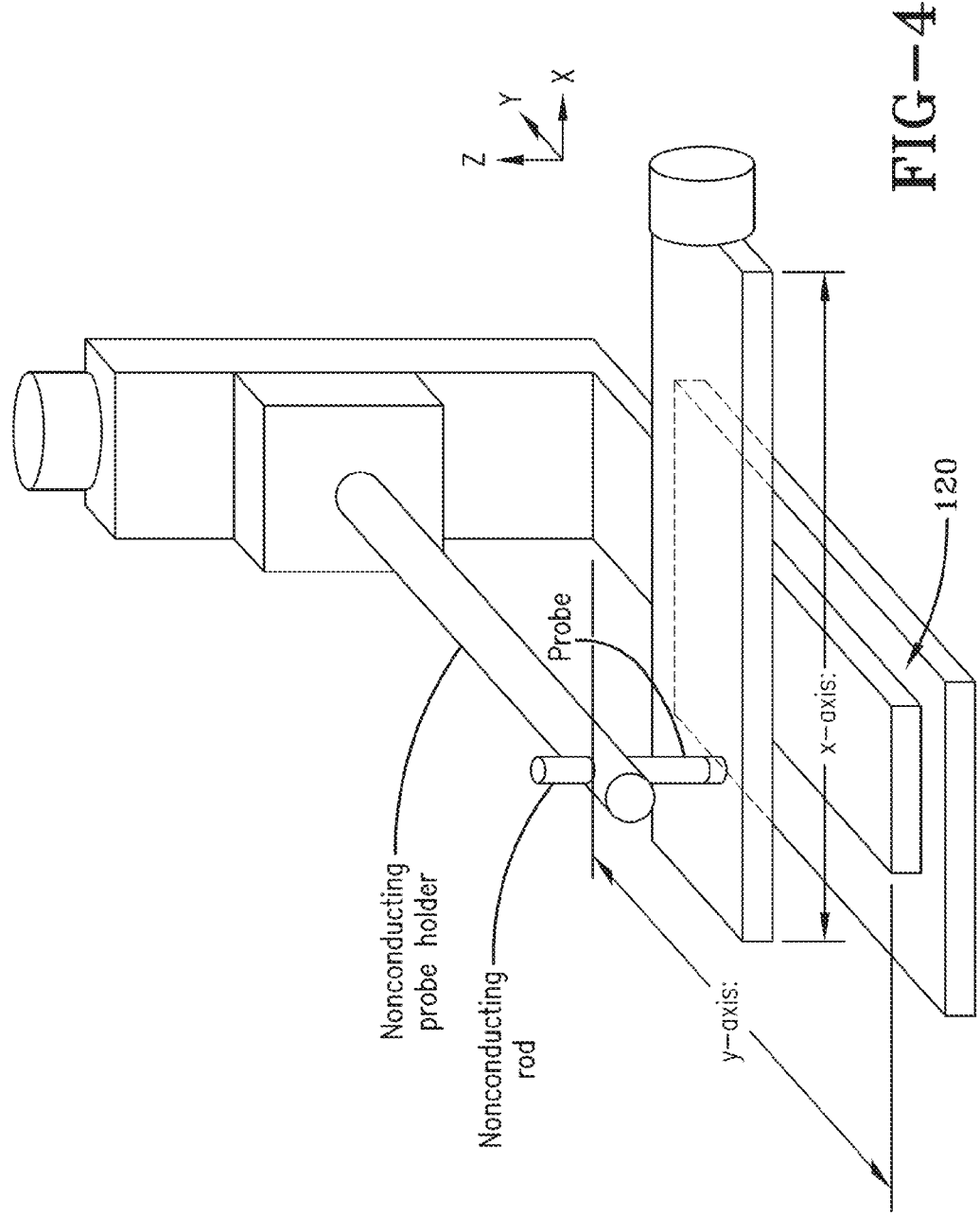

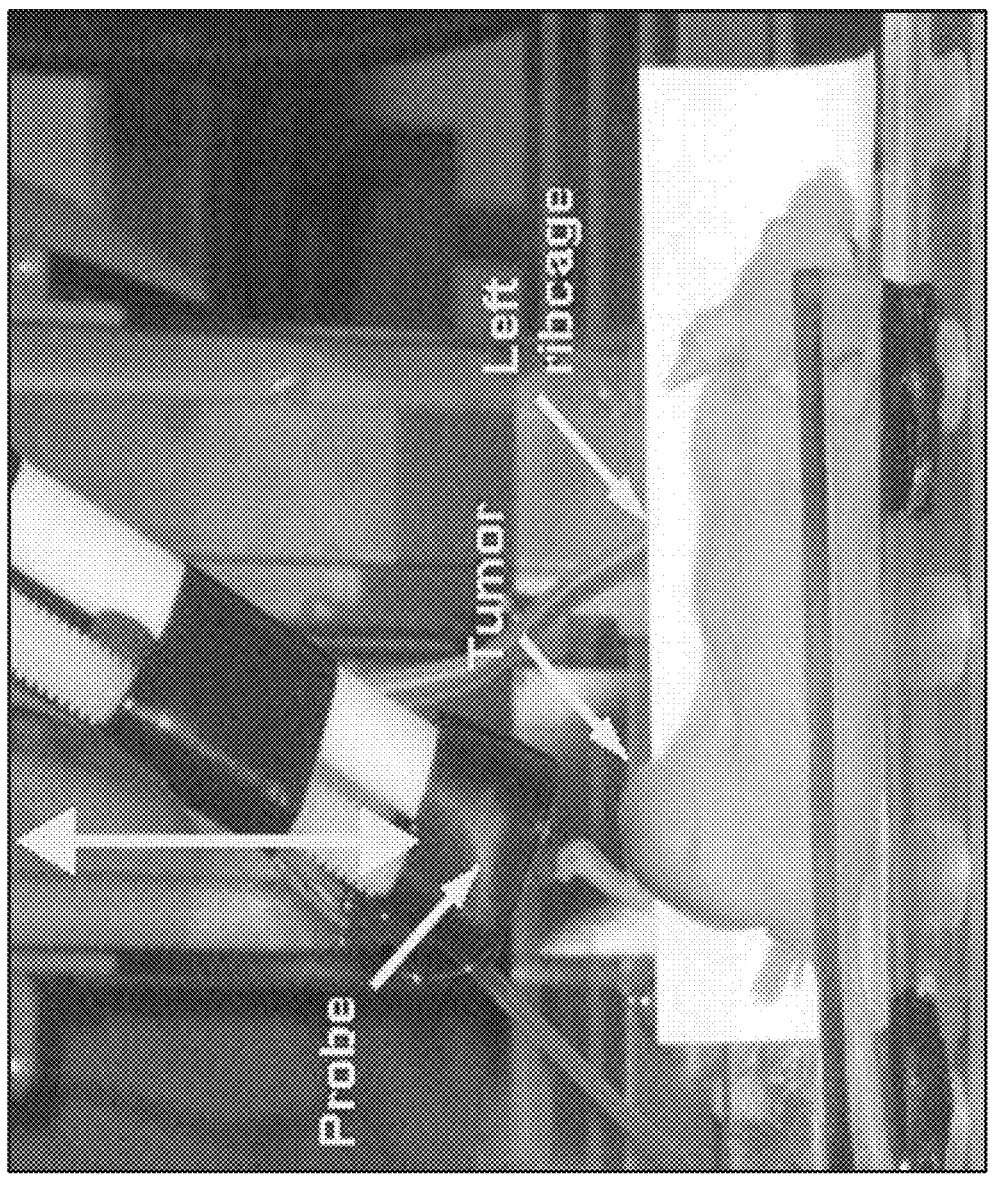

ELECTROMAGNETIC SYSTEM AND METHOD

CROSS-REFERENCE TO RELATED APPLICATIONS

This non-provisional application is a continuation-in-part of U.S. application Ser. No. 13/210,293, filed Aug. 15, 2011, which in turn claims the benefit of priority to the continuation of PCT/US2010/000444, filed Feb. 16, 2010, which in turn claims the benefit of priority to U.S. Provisional Application Nos. 61/152,408, filed Feb. 13, 2009, 61/234,745, filed Aug. 18, 2009, and 61/239,652, filed Sep. 3, 2009. Each of these applications is incorporated by reference as if fully recited herein.

TECHNICAL FIELD

Embodiments are directed to the fields of cancer biology and medicine. More particularly, it concerns systems, apparatuses, and methods for assessing abnormal tissue in an organism. Additionally, embodiments are broadly applicable for numerous electromagnetic detection applications, such as detection of minute quantities of metal in food.

BACKGROUND OF THE ART

Successful treatment of cancer often relies on surgery, which in turn depends on the accuracy of the detection and imaging tools available to the surgeon. Of the non-skin cancers diagnosed every year in the U.S., most (~50%) are cured by surgical resection. Only a small percentage of patients are cured by radiation therapy and chemotherapy, while the remainder are incurable. At present, patients undergoing planned cancer surgery with a curative intent depend upon pre-operative imaging techniques such as computer tomography (CT) scans, magnetic resonance imaging (MRI), and positron emission tomography (PET) scans for cancer detection. This pre-operative imaging is usually able to detect the primary tumor or tumors, but often fails to indicate the extent of metastasis. A technique is needed to provide the surgeon with real-time, dynamic, intraoperative information that could ultimately impact decision-making in the operating room (OR).

Accurate assessment of resection margins and detection of occult disease (including affected lymph nodes) during surgery is known to reduce recurrence rates and improve long-term patient outcomes. Of particular interest are detection techniques with the potential to be developed into intraoperative tools that could be used in the OR. Accordingly, development of an intraoperative probe is vital in the precise identification of occult tumor and for the evaluation of the adequacy of surgical resection margins in the OR, both of which presently rely on frozen sections and post-operative pathological examination. Such a technique could also serve to advance image-guided pathology.

SUMMARY

Various embodiments comprise an electromagnetic (EM) probe including of a pair of coils designed to detect changes in inductive coupling due to eddy currents when different materials are brought into the probe's vicinity. Experiments on human colon cancer-bearing xenograft mice and human tissue excised during cancer surgeries demonstrate the probe's consistent ability to differentiate between healthy and abnormal tissue. Various embodiments utilize sawtooth excitation of the tissue to achieve the greatest sensitivity. In various embodiments, the information contained in the phase shift of the induced voltage in the receiver coil relative to the voltage across the driver coil is substantially less ambiguous in detecting differences in tissue properties. Embodiments are appropriate for use in intraoperative detection of abnormal tissue conditions (e.g., cancer), and their selectivity may be further enhanced when used in conjunction with molecular targeting agents. The method may also be readily extended to imaging of surgically excised tissue and real-time tissue analysis in the operating room. Additionally, an exemplary method may also be extended for diagnosis of disease, post-surgical imaging to determine efficacy of surgery, or imaging to determine efficacy of therapeutic treatment (e.g. from chemotherapy, or hyperthermic treatment using conjugated nanoparticles (NP)).

In various embodiments, a novel, hand-held electromagnetic probe is disclosed for the detection of occult tumor and for the accurate assessment of surgical margins. In alternative embodiments, the probe is mechanically or robotically positioned. In some embodiments, the probe may be used in conjunction with a particle or tracer with electrical conductivity or magnetic properties that are distinguishable from the electrical conductivity or magnetic properties of the tissue, the particle or tracer operably linked or associated with a molecular targeting agent selective for an abnormal tissue (e.g., cancer).

Accordingly, embodiments include a method of identifying an abnormal condition occurring in a tissue of an animal, comprising:

providing a probe comprising a driver coil and a receiver coil;

positioning the probe adjacent to the tissue;

imposing a time-varying current or voltage through the driver coil at a fixed frequency;

measuring the alternating current or voltage produced in the receiver coil;

comparing the induction phase shift between the alternating current or voltage imposed through the driver coil to the alternating current or voltage produced in the receiver coil, thereby determining the induction phase shift response of the animal tissue at the fixed frequency;

comparing the determined induction phase shift response of the animal tissue at the fixed frequency to an induction phase shift response of a normal animal tissue at the fixed frequency; and identifying an abnormal condition occurring in a tissue based on the comparison. In various embodiments, the waveform of the alternating current or voltage is selected from the group consisting of square, triangle, and sawtooth waveforms.

In specific embodiments, the waveform of the alternating current or voltage comprises a sawtooth waveform.

In various embodiments, at least a portion of the driver coil is disposed within the cylinder defined by the receiver coil.

In some embodiments, the step of identifying an abnormal tissue comprises detecting a neoplasm.

In various embodiments, the tissue is selected from the group consisting of brain tissue, breast tissue, lung tissue, heart tissue, muscle tissue, skin tissue, kidney tissue, cornea tissue, liver tissue, pancreas, ovary, uterus, bone tissue, abdomen tissue, head tissue, leg tissue, arm tissue, pelvis tissue, chest tissue, and trunk tissue.

In some embodiments, the probe does not contact the animal tissue.

In various embodiments, the frequency of the alternating current or voltage is between about 1 Hz and about 1 MHz.

In some embodiments, the frequency of the alternating current or voltage is between about 1 Hz and about 100 kHz.

Some embodiments further comprise the steps of:

administering to the animal an effective amount of a particle or tracer with electrical conductivity or magnetic properties that are distinguishable from electrical conductivity or magnetic properties of the tissue (i.e., either higher or lower than tissue to be examined), conjugated with a molecular targeting agent, the molecular targeting agent selectively binds a marker associated with cells associated with an abnormal condition occurring in a tissue; and pausing after the administering step for a period sufficient to allow the unbound molecular targeting agent to clear.

In some embodiments, the molecular targeting agent comprises an antibody and the conductive particle comprises a nanoparticle.

Additional embodiments include a method of treating an abnormal condition occurring in a tissue of an animal, by exciting the conductive particles with EM waves to kill cells associated with an abnormal condition by hyperthermia after the targeting agent is bound to a marker associated with cells associated with an abnormal condition occurring in a tissue.

Other embodiments include a method of imaging an abnormal condition occurring in a tissue of an animal, comprising the steps of:

providing a probe comprising a driver coil and a receiver coil;

positioning the probe adjacent to the tissue;

imposing a time-varying current or voltage through the driver coil at a fixed frequency;

measuring the alternating current or voltage produced in the receiver coil;

comparing the induction phase shift between the alternating current or voltage imposed through the driver coil to the alternating current or voltage produced in the receiver coil, thereby determining the induction phase shift response of the animal tissue at the fixed frequency;

determining the induction phase shift response at various positions across the animal tissue at the measured frequency; and generating an image based on the induction phase shift response at various positions across the animal tissue.

Various embodiments include an arrangement for identifying an abnormal condition occurring in a tissue of an animal, comprising:

a probe comprising a driver coil and a receiver coil, at least a portion of the driver coil is disposed within the cylinder defined by the receiver coil;

an alternating current power supply connected to the driver coil, the alternating current power supply configured to generate a fixed frequency of a current or voltage in the driver coil;

a measurement system operably connected to the receiver coil, the measurement system is configured to measure a phase shift between the voltage or current imposed on the driver coil and the voltage or current produced in the receiver coil when the driver and receiver coils are positioned adjacent to the tissue; and a system for presenting the measured phase shift between the input voltage or current imposed on the driver coil and the alternating voltage or current induced in the receiver coil in order to identify the abnormal condition occurring in the tissue.

In various embodiments, the waveform of the alternating current or voltage is selected from the group consisting of square, triangle, and sawtooth waveforms.

In other embodiments, the waveform of the alternating current or voltage comprises a sawtooth waveform.

In some embodiments, at least a portion of the driver coil is disposed within the cylinder defined by the receiver coil.

In various embodiments, the frequency of the alternating current or voltage is between about 1 Hz and about 1 MHz.

In other embodiments, the frequency of the alternating current or voltage is between about 1 Hz and about 100 kHz.

In other embodiments, the arrangement further comprises: an effective amount of a particle or tracer with electrical conductivity or magnetic properties that are distinguishable from electrical conductivity or magnetic properties of the tissue (i.e., either higher or lower than tissue to be examined), conjugated with a molecular targeting agent, the molecular targeting agent is structured to bind a marker associated with cells associated with an abnormal condition occurring in a tissue.

In some embodiments, the molecular targeting agent comprises an antibody and the conductive particle comprises a nanoparticle.

In various embodiments, the alternating current power supply comprises: a function generator configured to generate an alternating current or voltage having a sawtooth waveform.

Alternative embodiments include a medical imaging apparatus comprising:

a probe comprising a driver coil and a receiver coil, at least a portion of the driver coil is disposed within the cylinder defined by the receiver coil;

an alternating current power supply connected to the driver coil, the alternating current power supply configured to generate a fixed frequency of a current or voltage in the driver coil;

a means for raster scanning the probe at various positions across the tissue; and a measurement system operably connected to the receiver coil, the measurement system is configured to measure phase shifts between the voltage or current imposed on the driver coil and the voltage or current produced in the receiver coils when the driver and receiver coils are positioned at locations across the tissue; and a system for presenting the measured phase shift between the input voltage or current imposed on the driver coil and the alternating voltage or current induced in the receiver coil at positions across the tissue in order to create an image.

Another embodiment includes a method of identifying an abnormal condition occurring in a tissue of an animal, comprising:

providing a probe comprising a coil;

positioning the probe adjacent to the tissue;

imposing a first time-varying current or voltage through the coil at a fixed frequency;

detecting a reflected time-varying current or voltage through the coil at a fixed frequency;

measuring the standing wave ratio between the first time-varying current or voltage and the reflected time-varying current or voltage, thereby determining an inductive reactance response of the coil at the fixed frequency;

comparing the inductive reactance response of coil for the animal tissue to the inductive reactance response of the coil for a normal animal tissue at the fixed frequency; and identifying an abnormal condition occurring in a tissue based on the comparison.

At least one embodiment includes a method of identifying an abnormal condition occurring in a tissue of an animal, comprising:

provide a probe comprising a coil;
positioning the probe adjacent to the tissue;
imposing a first time-varying current or voltage through the coil at a fixed frequency;
detecting a reflected time-varying current or voltage through the coil at a fixed frequency;
measuring a time period between the imposing step and the detecting step, thereby determining an inductive reactance response of the coil at the fixed frequency; comparing the inductive reactance response of the coil for the animal tissue to the inductive reactance response of the coil for a normal animal tissue; and
identifying an abnormal condition occurring in a tissue based on the comparison.

BRIEF DESCRIPTION OF THE DRAWINGS

A better understanding of the invention will be obtained by reference to the appended drawings, wherein identical parts are identified with identical reference numerals and wherein:

FIGS. 3A and 3B, respectively, illustrates one example graph of voltage signals from the driver and receiver coils; and is a schematic demonstrating the operation of an embodiment comprising a lock-in amplifier;

FIG. 4 is a schematic showing non-conducting probe holder and stage which control the placement and movement of the probe relative to the specimen, where motion in the x-, y- and z-directions is controlled by three separate motors that turn three separate threaded rods, causing motion either of the probe in the z-direction or of the non-conducting PLEXIGLAS stage in the x- or y-direction, with non-conducting materials are used to prevent any interference with the probe signal FIG. 5 shows the experimental set-up for in vivo measurements on an animal model;

DETAILED DESCRIPTION

Figures 1A, 1B:
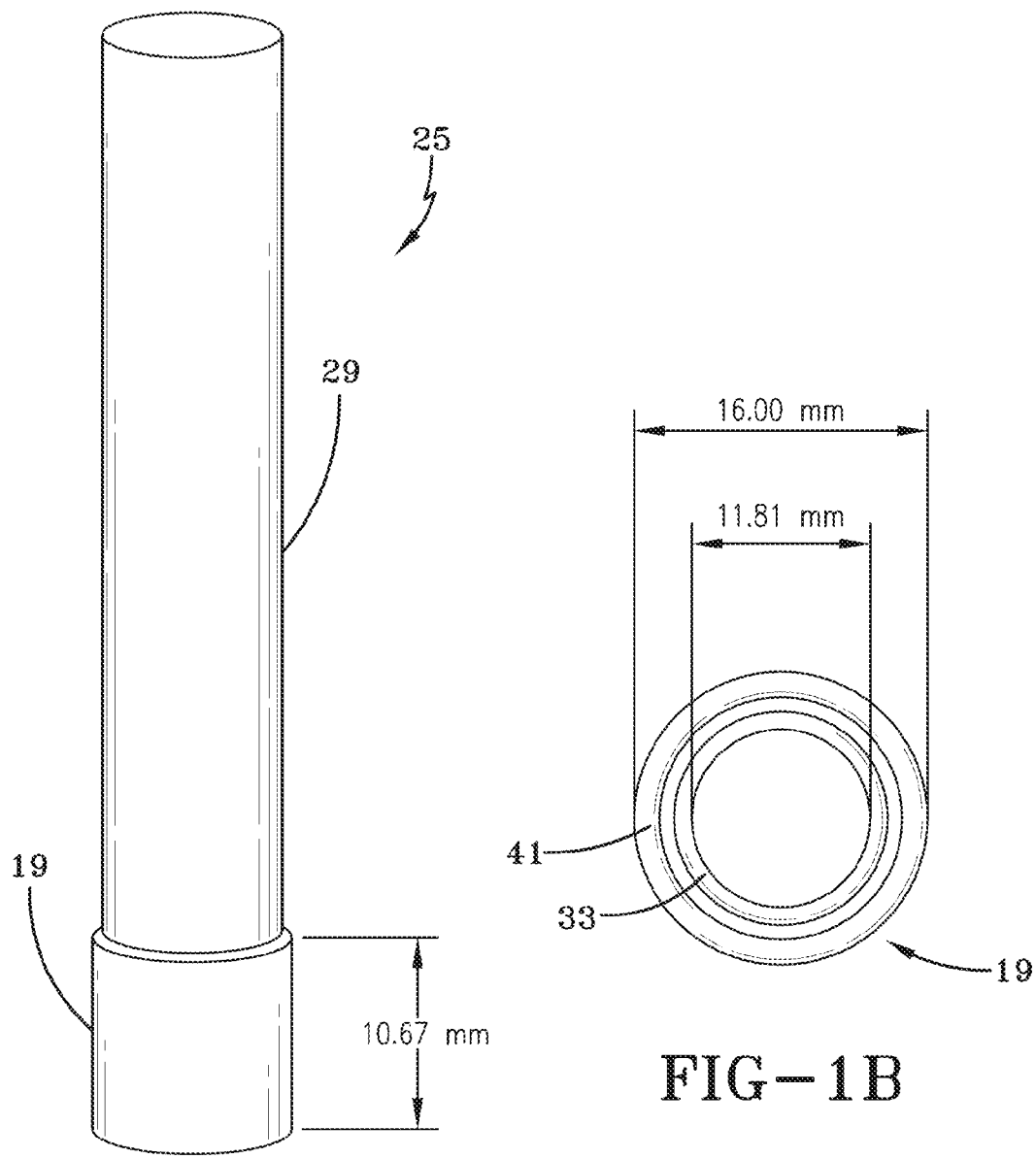
FIGS. 1A and 1B are, respectively, a schematic of an electromagnetic probe used for measurement of magnetic susceptibilities of tissue and a bottom plan view of an exemplary embodiment with two concentric coils.

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

As used herein, the phrase "operably connected" may be intended to mean coupled or connected, either directly or indirectly, such that the connected structures are operable to perform a desired function.

As used herein, the word "animal" broadly refers to all members of the kingdom Animalia, including humans. Other animals include vertebrates such as fish and other mammals such as mice, rats, rabbits, cats, dogs, pigs, cows, ox, sheep, goats, horses, monkeys and other non-human primates.

Embodiments include a system and a method for detecting an abnormal condition in an animal tissue. Exemplary embodiments comprise an EM probe operating in the kHz range and consisting of a pair of parallel-axis, multi-turn coils, one used as a driver and one as a receiver. In a preferred embodiment, phase-sensitive detection may be provided by a lock-in amplifier. The lock-in amplifier measures the phase shift of the receiver coil signal relative to that of the reference input, which is the signal from the function generator that is used as an input to the driver coil. In an exemplary embodiment, the phase shift between the alternating voltage or current imposed on the driver coil and the alternating voltage or current induced in the receiver coil may be used to detect changes in the EM properties of tissue brought into its vicinity.

An exemplary embodiment may be used to detect cancerous or pre-cancerous tissue in an animal (e.g., humans and or other mammals), for example, intra-operative cancer detection. The system and method exploit differences in the electromagnetic (EM) properties between abnormal and normal tissue (e.g., cancerous and healthy tissue). More specifically, by way of time-varying EM fields, electrical eddy currents are generated in tissue samples, and assessed using phase-sensitive detection. Embodied methods and systems utilize the change in phase shift between the voltage in a receiver coil and the voltage in a driver coil to provide a direct and immediate indication of differences in EM properties of specimens.

In an exemplary embodiment, the presence of additional, symmetric detector coils is not necessary to establish a null condition. Instead, various embodiments use a reference phase of a lock-in amplifier to null the device. Preferred embodiments utilize a function generator to impose alternating driving voltages or currents, preferably non-sinusoidal driving voltages or currents (e.g., square, triangle, sawtooth, etc), more preferably sawtooth-type driving voltages or currents, at frequencies between 1 Hz and 1 MHz, more preferably between 1 Hz and 100 kHz (e.g. 99 kHz) through a driver coil. When different materials are brought into the probe's vicinity, imposing such low frequency, non-sinusoidal driving signals through the driver coil may produce induced phase shifts as much as 60 times greater than those produced by sinusoidal excitation. The physics underpinning the extreme phase shifts is unknown.

In an exemplary embodiment, the probe diameter may be constructed to approximate the anticipated size of the tissue eddy current diameters (e.g., millimeters) or smaller. Additionally, the EM probe need not contact the relevant tissue in order to perform the examination. Embodiments have been successfully used to detect cancer in both a xenograft mouse model and in surgically excised tissue from cancer patients.

The following embodiments are included as representative examples. It should be appreciated by those skilled in the art that the systems, devices, and methods disclosed in the examples which follow, represent systems, devices, and methods that function well in the practice of the invention, and thus can be considered to constitute acceptable modes for its practice. However, those of skill in the art should, in light of the present disclosure, appreciate that many changes can be made in the specific embodiments which are disclosed and still obtain a like or similar result without departing from the concept, spirit, and scope of the invention. Additionally, it will be apparent that certain agents both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Referring to FIG. 1A, an exemplary embodiment comprises an EM probe 25. The probe may comprise a probe head 19 affixed to a support 29. In one embodiment, the probe head 19 may be about 10.67 mm long. Referring to FIG. 1B, the EM probe of an exemplary embodiment may comprise two concentric coils of wire. The coils may be concentrically wound using insulated copper wire (e.g., 32 gauge (0.202 mm diameter)). The (inner) driver coil 33 may contain two layers of evenly-wound turns, while the (outer) receiver coil 41 may be made up of five layers and be scatter wound. The inner diameter of the driver coil 33 may be 11.81 mm, and the outer diameter of the receiver coil may be 16.00 mm. Accordingly, in this embodiment the outer diameter of the driver coil 33 is calculated to be 12.62 mm based on the thickness of the wire. In some embodiments, the probe is a hand-held instrument. In alternative embodiments, the probe is mechanically or robotically positioned.

Figure 2:
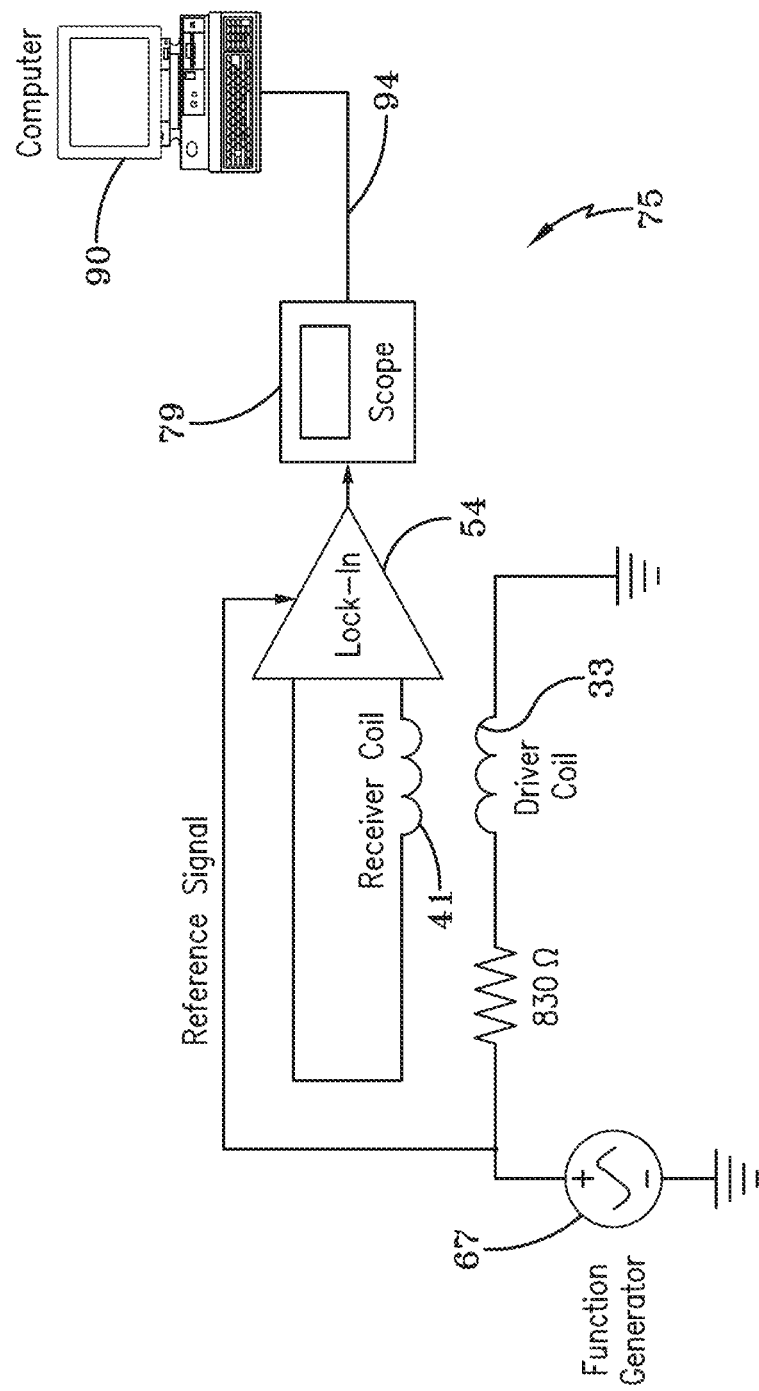
FIG. 2 is a schematic of the driving and data acquisition system of an embodiment.

Referring to FIG. 2, the EM probe of an exemplary embodiment may be operably connected to a driving and data collection system 75. FIG. 2 shows a schematic of an exemplary system. In the embodiment shown, the driver side of the probe comprises a function generator 67 (e.g., HP 33120A from Hewlett-Packard, Loveland, Colo.), which may provide both the driving signal ($f_{in}$) to the driver coil 33 and the reference signal ($f_{reference}$) to the lock-in amplifier 54. In this embodiment, the AC voltage in the driver coil 33 imposes a current that induces a voltage in the receiver coil 41. A lock-in amplifier 54 (e.g., models SR510 (single channel) or SR 530 (dual channel), Stanford Research Systems, Sunnyvale, Calif.) may be used to amplify the voltage from the receiver coil 41 at a fixed phase. In an exemplary embodiment, the presence in close proximity of a material with different electromagnetic properties (a tissue sample containing a tumor, for example) changes the mutual inductance between the driver and receiver coils and leads to a different reading at a fixed phase.

Referring again to FIG. 2, the driving signal to the driver coil 33 of the probe and the reference input to the lock-in amplifier 54 are provided by a function generator 67. In an exemplary embodiment, function generator is used to drive a predetermined waveform through the driver coil. Preferably, the waveform generator drives a sawtooth waveform through the driver coil. For example, in one preferred embodiment, the waveform generator 67 imposes an alternating voltage of a 7 Vpp sawtooth waveform at a fixed frequency of 99 kHz through the driver coil 33. Advantageously, imposing a sawtooth waveform yields an unexpectedly greater voltage change on the receiver than sinusoidal excitation of the driver. The function generator 67 may also be used to drive other waveforms, for example, a square or triangle waveform through the driver coil.

The signal from the receiver coil is sent to a lock-in amplifier 54 (e.g., Stanford Research Systems, Sunnyvale, Calif.). The output from the lock-in amplifier is captured by an oscilloscope 79 (e.g., Agilent 54622A, 100 MHz, oscilloscope). In an exemplary embodiment, the oscilloscope 79 output may be transferred over a data cable 94 to a computer 90. This data may be captured by a computer 90 programmed with specialized software, for example, Agilent Intuilink 54600 Scope Control software (ver. 2.0.0). Preferably, this software allows for the scope data to be transferred to a text file, excel file, or saved as an image, that may be saved and analyzed. In some embodiments, the oscilloscope 79 may be omitted from the data collection system 75 by programming the computer 90 with appropriate data collection software.

The operation of an exemplary EM probe with respect to the lock-in amplifier 54 is illustrated in FIG. 3. FIG. 3(a) shows the voltage signals from the driver and receiver coils. The voltage from the driver coil $V_d = E_0 \cos(\omega t + \phi_{ref})$ is used as the reference signal, while the voltage from the receiver coil $V_r = V_0 \cos(\omega t + \delta)$ is the input signal. The reference phase $\phi_{ref}$ of $V_d$ may be adjusted during operation of the lock-in amplifier. FIG. 3(b) details the operation of a single channel lock-in amplifier, such as the SR510. The signals $V_d$ and $V_r$ are passed through a multiplier 102. The product of two cosines of frequency ω is equal to the sum of two cosines, one having a sum frequency (ω+ω) and the other having a difference frequency (ω−ω). The sum frequency component is strongly attenuated by a low-pass filter (LPF) 107. Because the frequencies of the driver and receiver coils are equal, the cosine of the difference term simply yields a DC output proportional to $\cos(\phi_{ref} - \delta)$. This DC output is sent though a DC amplifier 113. Therefore, the DC output voltage $V_{out}$ is proportional to the product of the magnitudes of $V_d$ and $V_r$ and the cosine of the phase difference between them, that is, $V_{out} = GE_0 V_0 \cos(\phi_{ref} - \delta)$, where G is the total gain from the lock-in amplifier. Initially, the reference phase $\phi_{ref}$ is adjusted such that the phase difference between the two signals is π/2, which sets $V_{out}$ to zero. When a specimen is brought into proximity of the coils, the mutual inductance between the two coils changes. Inductive interaction between the coils that form the probe head and the eddy currents that arise in the specimen introduce both a phase and a magnitude change in the receiver coil signal $V_r$ and lead to a nonzero value of $V_{out}$. The phase change can be measured directly from a single channel lock-in amplifier using the null method. The reference phase $\phi_{ref}$ is adjusted to achieve a DC output of zero with no specimen present. Once the specimen is brought into the vicinity of the probe, $\phi_{ref}$ is adjusted again to re-establish the null condition and the difference between the two values of $\phi_{ref}$ is the phase shift due to the presence of the specimen.

A dual channel lock-in amplifier (SR530) operates on the same principle, but with an added step that allows it to measure the phase directly without using the null method. The signal $V_r$, in addition to being multiplied by $\cos(\omega t + \phi_{ref})$, is also multiplied by $\sin(\omega t + \phi_{ref})$ in a separate channel. The resulting sum frequency is attenuated as before by a LPF. The result is two DC outputs, one proportional to $\cos(\phi_{ref} - \delta)$ and one proportional to $\sin(\phi_{ref} - \delta)$. These signals are $$V_1 = GV_0 \cos(\phi_{ref} - \delta) \qquad (1)$$

$$V_2 = GV_0 \sin(\phi_{ref} - \delta) \qquad (2)$$

where G is a gain. The magnitude of the input to the lock-in amplifier (i.e. output from the receiver coil) is therefore $V_0 = \sqrt{V_1^2 + V_2^2}/G$, and the phase response is $$\delta = -\tan^{-1}\left(\frac{V_2}{V_1}\right)$$

[Stanford Research Systems, 2001]. If the reference phase $\phi_{ref}$ is adjusted so that the phase of the input signal δ is zero with no specimen present, then the phase shift due to placement of the specimen in the vicinity of the probe can be read directly from the dual-channel lock-in amplifier.

Referring to FIG. 4, in an exemplary embodiment, the motion of the probe relative to the specimen may be aligned by way of an adjustable stage 120. Various embodiments utilize a commercial milling machine, for example, a MaxNC CL2 precision 3-axis milling machine (e.g., MaxNC, Gilbert, Ariz.). The MaxNC CL2 controlling software is run from a 2000 P5-90 Pentium computer running DOS. A 38 cm long non-conducting holder made of PVC was constructed to hold the probe, which is attached to the end of a non-conducting nylon rod which holds the probe 10 cm below the probe holder. The probe and its holder are moved up and down in the z-direction by the z-axis motor on the MaxNC. Two other motors control motion in the x- and y-directions. A 40×18 cm nonconducting plexiglass stage is fastened to a platform on the MaxNC that is capable of motion in the x- and y-directions. Motion in all three directions is achieved by using one of three motors to turn one of three threaded rods, causing the appropriate platform to move in the desired direction. The threaded rod controlling motion in the z-direction is 40 cm long, while those controlling motion in the x- and y-directions are 44 and 30 cm long, respectively. Non conducting materials are used to hold the probe and specimen to prevent any interference with the probe signal by the metal parts that make up the MaxNC.

In Vivo Detection of Cancer in an Animal Model Using an Exemplary EM Probe

An embodiment comprising two concentric coils successfully detected cancerous tissue in vivo in animal models, using phase-sensitive detection. Experimental measurements with the probe were also conducted with animal models injected with 5 nm iron oxide NPs and antibody-NP (i.e. NP-CC49) conjugates. Measurements in the animal models with the antibody-NP conjugates were performed to explore the potential for improving selectivity of the measurement. Additional measurements on 5 nm NPs of iron oxide in phantoms were also conducted to identify other characteristics of the measurement technique.

Although not required, various embodiments include the additional step of administering to the animal an effective amount of a particle or tracer with electrical conductivity or magnetic properties that are distinguishable from the electrical conductivity or magnetic properties of the tissue (i.e., either higher or lower than tissue to be examined). In various embodiments, suitable particles or tracers may include, for example, but not limited to, iron oxide NPs, gold NPs, polyethylene glycol (PEG). The particle or tracer may be conjugated with a molecular targeting agent. In various embodiments, suitable molecular targeting agents include, for example, but not limited to, peptides, lectins, antibodies (monoclonal and polyclonal), aptamers, avimers, etc. In exemplary embodiments, the molecular targeting agent selectively binds a marker associated with cells associated with an abnormal condition occurring in a tissue. An exemplary embodiment comprises administering to a patient an effective amount of a molecular targeting agent which specifically binds a marker produced by or associated with an abnormal tissue (e.g., neoplastic tissue). The dosage of the molecular targeting agent is such that the EM detection arrangement can be utilized for determining sites exhibiting accretion of the labeled targeting agent (e.g., neoplastic tissue or cells). Molecular targeting agent dosages may depend upon the specific type of molecular targeting agent used, the electrical conductivity or magnetic properties of the particle or tracer conjugated to targeting agent, the characteristics of the excitation signal used to excited the particle or tracer, the sensitivity of the detection equipment, and other factors which may affect dosage requirements as those skilled in the art will appreciate.

If a labeled targeting agent is utilized, the immediate accession of a subject with embodied electromagnetic detection arrangements is not advisable. Preferably, time is permitted to elapse following administration of the targeting agent in order for unbound targeting agent to be cleared from the tissue surrounding the tissue to be surveyed. The clearance time may be as short as a few minutes on up to several weeks, depending upon how fast the subject's body clears (often metabolizes) the targeting agent.

Once a suitable interval has elapsed, the subject may be accessed with the electromagnetic detection instrument. The relevant sites may be surveyed with the electromagnetic detection instrument for determining accretion of the particle or tracer-labeled targeting agent by detecting with the instrument altered electrical conductivity or magnetic properties that are distinguishable from the electrical conductivity or magnetic properties of the tissue at the relevant sites.

The methods and detection arrangements disclosed may be used in conjunction with other existing modalities of cancer detection and imaging such as computed tomography, MRI, etc. For example, preoperative images of the surgical site acquired by other imaging modalities may be used by the disclosed arrangements for image reconstruction in order to enhance the accuracy and the depth resolution for intraoperative tumor detection.

The detection compositions of various embodiments may be administered systemically, non-systemically, locally or topically, parenterally as well as non-parenterally, e.g. subcutaneously, intravenously, intramuscularly, perorally, intranasally, by pulmonary aerosol, by injection or infusion into a specific organ or region, buccally, intracranically or intraperitoneally.

Effective amounts and regimens for the administration and detection of the molecular targeting agents according to the disclosed embodiments can be determined readily by those with ordinary skill.

(a) Preparation of the CC49-Nanoparticle Conjugate

CC49 is the murine form of a monoclonal antibody that targets the tumor associated glycoprotein TAG-72. A volume of 0.8 mL of the iron oxide stock solution (3 mg/mL) was transferred to a vial and diluted with 0.6 mL of PBS. While stirring continuously, 0.4 mL of 2-(N-morpholino) ethanesulfonic acid (MES) solution (0.5 M) (Sigma-Aldrich, St. Louis, Mo.) was added to the iron oxide solution, followed by addition of 0.1 mL of freshly prepared 1-ethyl-3-(3-dimethylamino propyl)carbodimidehydrochloride (EDC) PBS solution (7.6 mg/mL) (Sigma-Aldrich, St. Louis, Mo.) and 0.1 mL of freshly prepared sulfo-N-hydroxysuccinimide (sulfo-NHS) PBS solution (21.5 mg/mL) (Sigma-Aldrich, St. Louis, Mo.). The mixed solution was stirred for 20 minutes at room temperature and then passed through a 2 mL Zeba desalt spin column (Pierce Biotechnology, Inc., Rockford, Ill.). Next, 0.5 mL of CC49 solution (11 nmol CC49) (National Cancer Institute, Bethesda, Md.) was added to the eluted solution. The pH was adjusted to 8 with 150 μL Na$_2$CO$_3$ (0.01M). The mixed solution was stirred for 2 hours, and then the reaction was quenched by adding 2 mg of PEG-amine (MW 5000D) (Nanocs, Inc., New York, N.Y.). The solution was concentrated to 0.5 mL in a 30 kD cut-off centrifuge filter (Millipore, Billerica, Mass.) and loaded into a Superdex-200 column (GE Healthcare, Piscataway, N.J.), where it was eluted with PBS. The first eluted component was the CC49-nanoparticle conjugate.

(b) Animal Model (i) Cell Line

Human colon adenocarcinoma cells (LS174T) were obtained from the American Type Culture Collection (Manassas, Va.) and cultured in Dulbecco's modified Eagle high glucose medium (DMEM) supplemented with 10% fetal bovine serum (FBS) and 1% penicillin-streptomycin (Invitrogen Life Technologies, Carlsbad, Calif.). The cells were maintained in a humidified atmosphere of 5% CO$_2$ at 37° C., with the medium changed every other day. A confluent monolayer was detached with 0.05% trypsin-EDTA (Invitrogen Life Technologies, Carlsbad, Calif.) and dissociated into a single-cell suspension for further cell culture.

(Ii) Tumor Xenografts and Animal Preparation

Animal procedures were performed according to a protocol approved by the University Committee for the Use and Care of Animals (UCUCA) at The Ohio State University. Female athymic nude mice (nu/nu), obtained from National Cancer Institute (Bethesda, Md.) at 4-6 weeks of age, were subcutaneously inoculated in the back with approximately 5×10$^6$ LS174T cells suspended in a mixture of 50 μL of PBS and 50 μL of matrix gel basement membrane (BD Biosciences, San Jose, Calif.). When the tumors reached 0.4-0.6 cm in diameter (10 days after implantation), the tumor-bearing mice were injected with solutions of either Fe$_2$O$_3$ NPs or CC49-Fe$_2$O$_3$ conjugate. One tumor-bearing mouse was not injected with any solution and used as a blank control. Two tumor-bearing mice were intravenously injected with 0.1 mL and 0.2 mL of Fe$_2$O$_3$ NP solution (0.3 mg/mL) through the tail vein, respectively. The other tumor-bearing mice were intravenously injected with 0.1 mL and 0.2 mL of CC49-nanoparticle conjugate solution through the tail vein. All mice were subjected to measurements with the electromagnetic probe in vivo on days 3, 4, 5 and 8 after injection with the NPs.

(c) Electromagnetic Probe

In the embodiment tested, the probe was constructed as described above. Briefly, the detection probe comprises two parallel-axis coils of wire, one of which serves as a driver and the other as the detector. For these experiments, an alternating voltage of 7 Vpp (sawtooth-type) was imposed on the driver coil at a fixed frequency of 99 kHz and phase (~38°). A current of equal frequency is induced in the detector coil. A phase-lock amplifier is used to measure the out-of-phase component of the detector coil voltage with respect to the driver coil (see FIG. 1). The probe is nulled (zeroed) in air with nothing placed in front of it by adjusting the phase on the lock-in amplifier. When the end of the detector coil is brought either into contact with or within the vicinity of a material (such as healthy tissue or cancerous tissue), the mutual inductance between the driver and detector coils is altered, resulting in a change in the voltage induced in the detector coil and hence the voltage reading recorded on the lock-in amplifier.

(d) Experimental Design and Data Analysis (i) Experiments with Mice

As shown in FIG. 5, the electromagnetic probe was suspended above the anaesthetized animal and oriented at an angle approximately 20° from the vertical. This was done to ensure that the area of tissue interrogated by the probe was as small as possible, yielding a point-wise measurement. The receiver coil was brought at a constant speed of 2.1166 mm/s into contact with the target area, held in place until a steady voltage was displayed, then retracted from the sample and allowed to reach a steady reading once again. This process was repeated three times for each measurement, with a precision, 3-axis motorized stage controlling the probe's motion as described in FIG. 4. Despite the precision of the stage, it must be pointed out that it was not possible to ensure that the very same point on the animal was probed with each repeated measurement. Therefore, repeatability at a given location on a given animal could be guaranteed only to within millimeters. On each day of the measurements, the mice were anesthetized with Ketamine (100 mg/kg) (Hospira, Inc., Lake Forest, Ill.)/Xylazine (10 mg/kg) (VEDCO, Inc., St. Joseph, Mo.). Measurements were undertaken three times (three readings for each measurement) on the tumor for each animal, with each measurement involving removing the animal from the stage and replacing it after the previous measurement. Similarly, measurements below the left ribcage were used as representative readings indicative of healthy tissue for each animal. The lower left ribcage was chosen to avoid the liver, which was expected to be a site of uptake for NPs. The soft abdominal region was also rejected as representative of healthy tissue since the anesthetic was injected into the abdominal cavity and could potentially interfere with the probe readings.

Measurements were conducted on mice on the $3^{rd}$, $4^{th}$, $5^{th}$ and $8^{th}$ day after injection of the NPs, corresponding to 13, 14, 15, and 18 days after injection of the human colon cancer cells, respectively. The results of the nine probe measurements on both the tumor and the healthy tissues were averaged for each animal for each day. The averaged values are presented as a function of time (measured in days), along with the high and low voltage values recorded for each day.

(e) Experimental Results

Probe measurements recorded on the animal models are presented in FIGS. 6 through 8B. The average reading of the nine measurements is plotted on each day for both tumor and healthy tissue. The uncertainty bars indicate the range of readings collected per site per day. They are meant to give an indication of our ability to return to the same given location on the animal and do not indicate experimental measurement error. The actual experimental measurement error is smaller than the size of the data markers on the figures.

Figure 6:
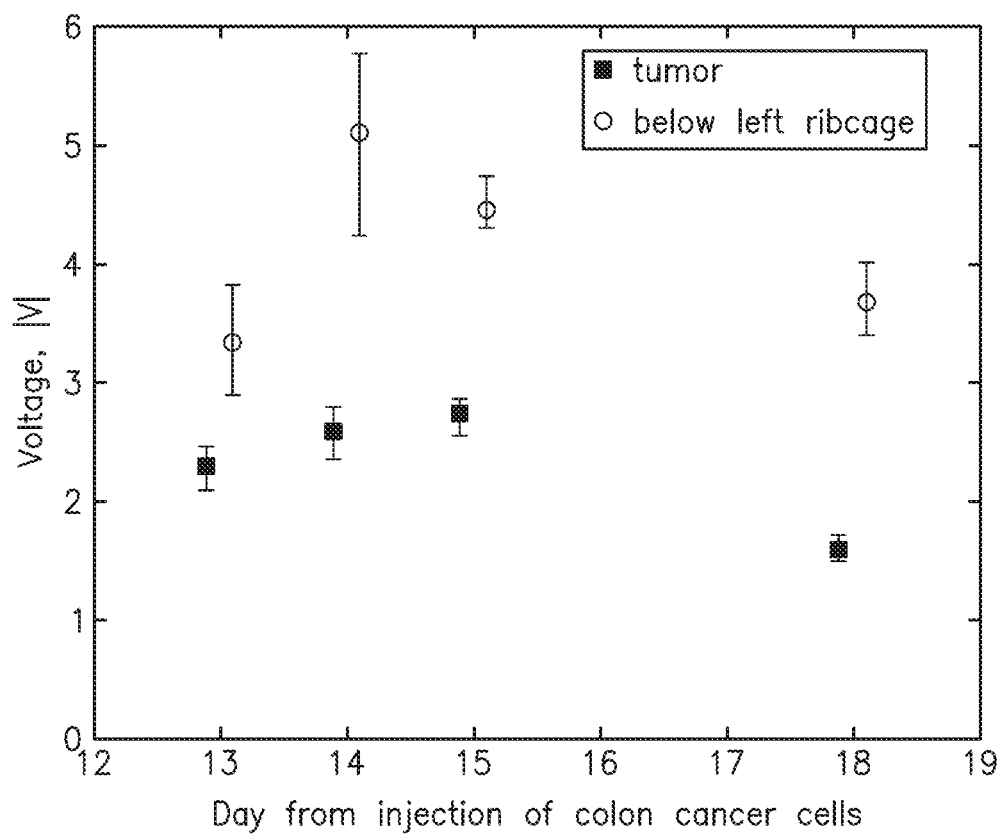
FIG. 6 shows electromagnetic probe readings on control animal, i.e., one injected with cancer cells but without any nanoparticles or antibodies, as a function of day from injection of colon cancer cells, with filled squares indicating measurements on the tumor, while open circles denote measurements on the lower left ribcage, denoting healthy tissue.
Figure 7A:
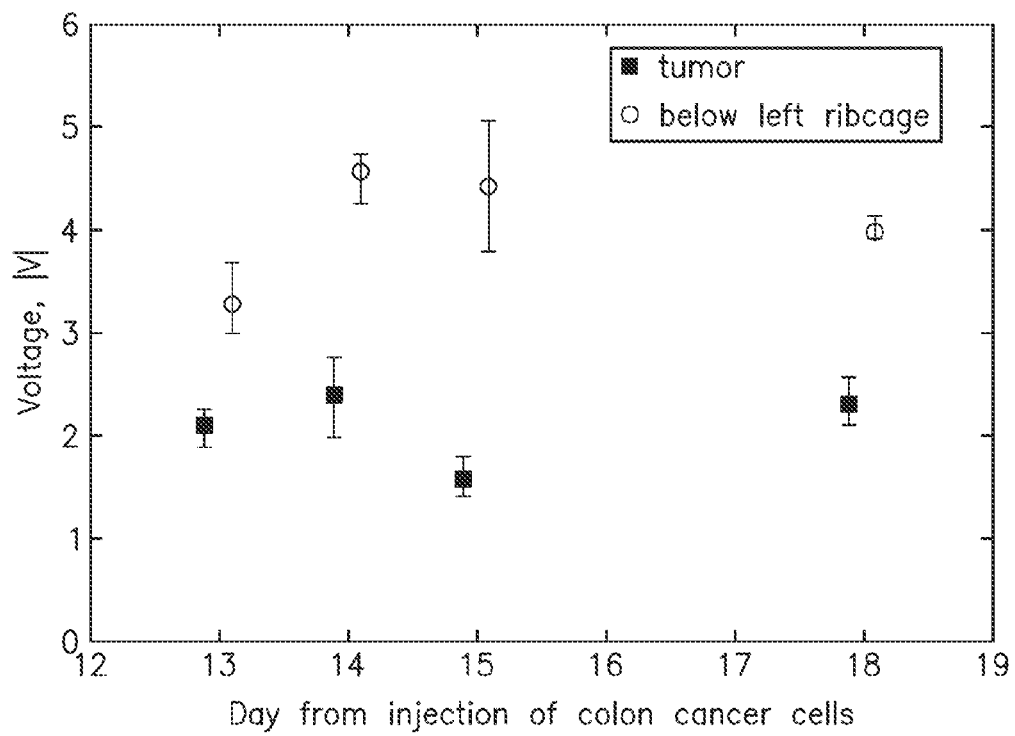
FIGS. 7A and 7B, respectively, show electromagnetic probe readings on an animal injected with 0.1 mL free $Fe_2O_3$ NPs (i.e., not conjugated to CC49) as a function of day from injection of colon cancer cells, where filled squares indicate measurements on the tumor while open circles denote measurements on the lower left ribcage, denoting healthy tissue; and electromagnetic probe readings on a mouse injected with 0.2 mL free (not conjugated to CC49) $Fe_2O_3$ NPs as a function of day from injection of colon cancer cells, where filled squares indicate measurements on the tumor while open circles denote measurements on the lower left ribcage, denoting healthy tissue.
Figure 7B:
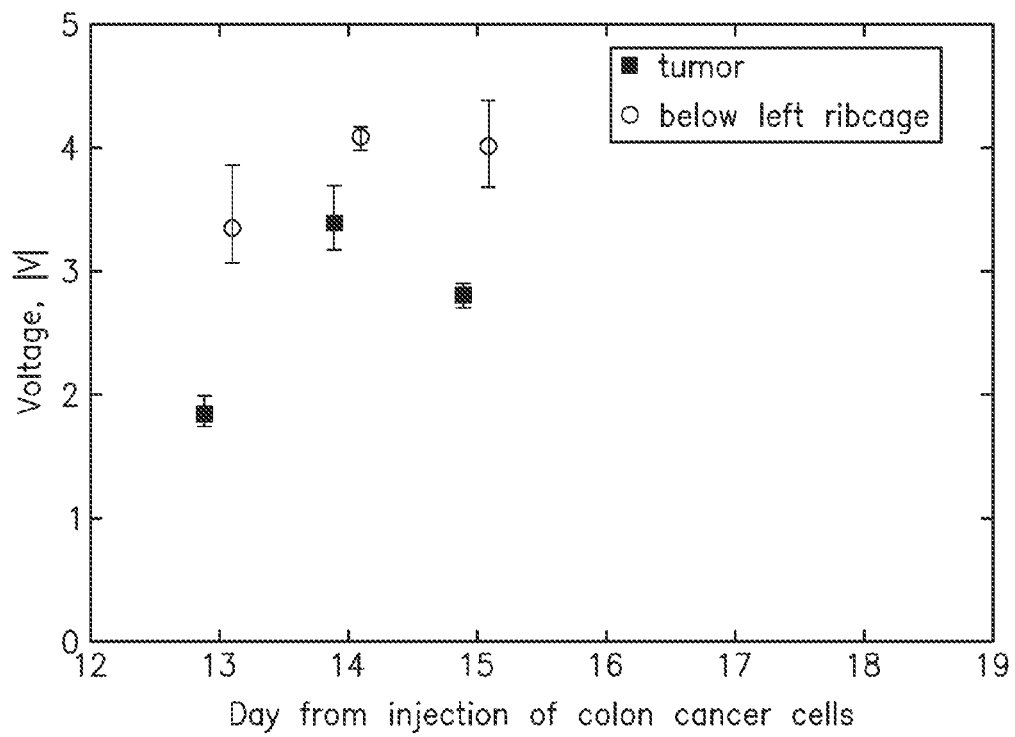
Figure 8A:
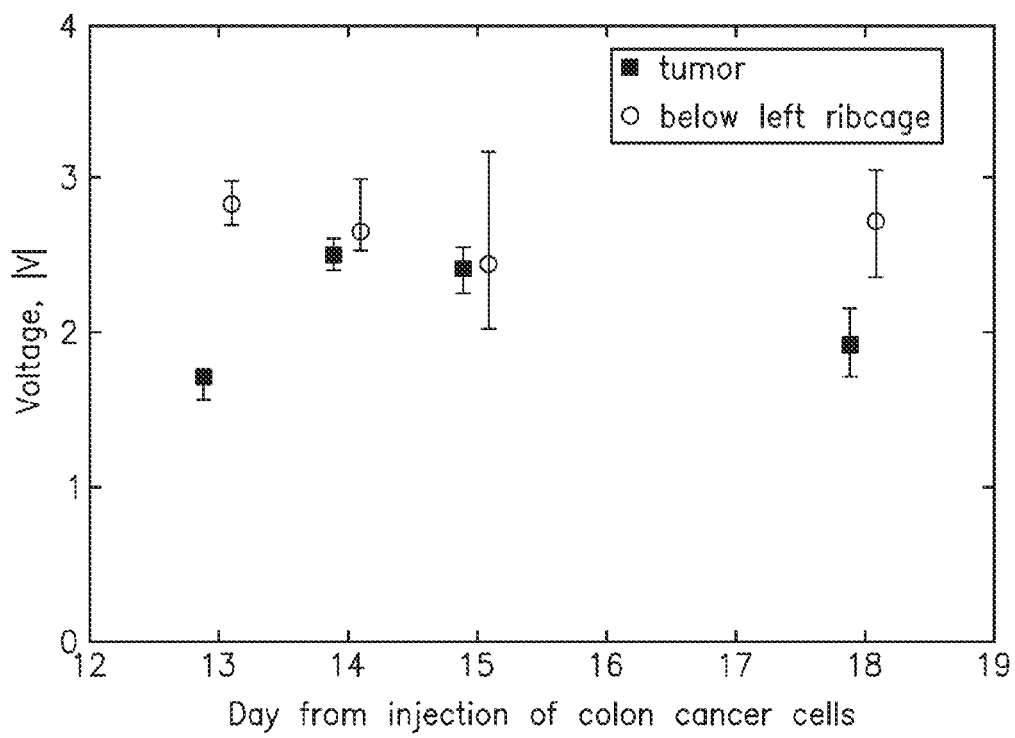
FIGS. 8A and 8B, respectively show electromagnetic probe readings on a mouse injected with 0.1 mL CC49-$Fe_2O_3$ solution as a function of day from injection of colon cancer cells, where filled squares indicate measurements on the tumor while open circles denote measurements on the lower left ribcage, denoting healthy tissue, and electromagnetic probe readings on a mouse injected with 0.2 mL CC49-$Fe_2O_3$ solution as a function of day from injection of colon cancer cells, where filled squares indicate measurements on the tumor while open circles denote measurements on the lower left ribcage, denoting healthy tissue.
Figure 8B:
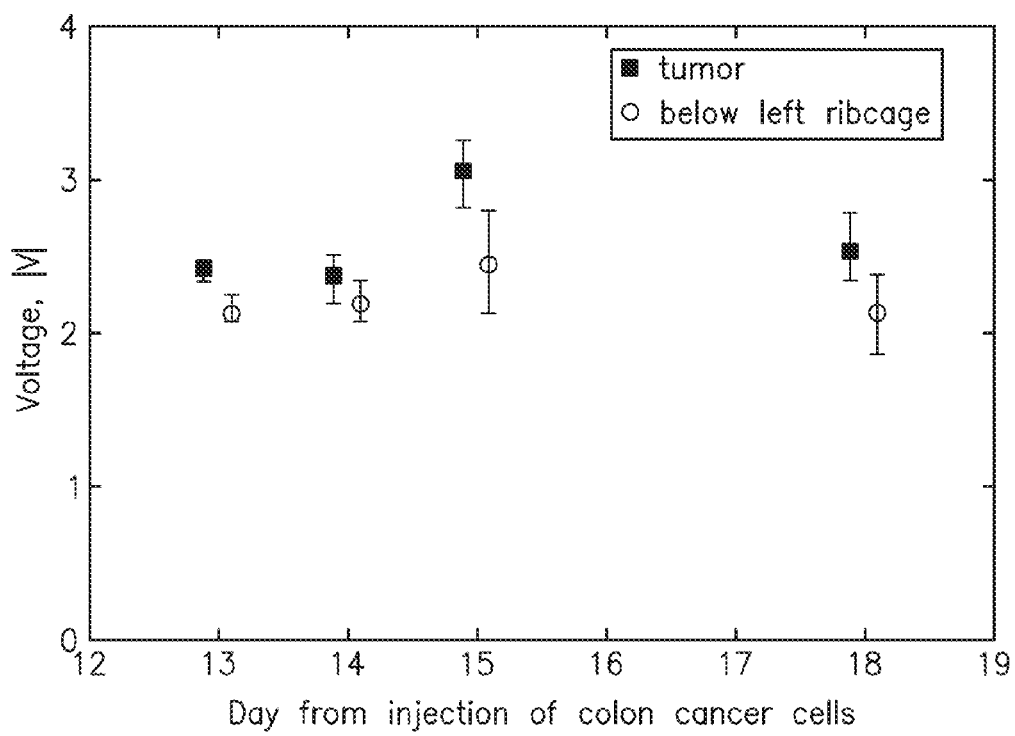

FIG. 6 shows results for the control animal, i.e. one injected with cancer cells but without any NPs or antibody. Note that in the absence of NPs, the tumor gives a noticeably different (in this case, lower) reading than the healthy tissue for all four days on which the measurements were made. It is important to stress that the significance of the results shown in FIG. 6 is not that the voltage recorded from the tumor is smaller, but that it is different from that of the non-cancerous tissue. It is certainly possible for the recorded voltage from the tumor to be higher than the healthy tissue used for comparison, since the measurement is phase-sensitive and the phase of the voltage in the detector coil could lag or lead, thereby leading to higher or lower recorded voltages. FIGS. 7A and 7B show results for the animals injected with suspensions of Fe$_2$O$_3$ NPs only at doses of 0.1 mL and 0.2 mL (0.3 mg/mL), respectively. As can be seen in these figures, even though the recorded voltage varies each day, the tumor still displays a noticeably different voltage compared to the healthy tissue. No measurements were recorded on day 18 for the animal in FIG. 7B because it died after day 15. FIGS. 8A and 8B show the results for the animals injected with 0.1 mL and 0.2 mL of solution containing the antibody CC49 conjugated with the $Fe_2O_3$ NPs, respectively. As with the previous results, the voltages recorded from the tumor for the lower dose case (0.1 mL) are different and lower compared to those obtained from the healthy tissue. However, note that the tumor gives a comparable or higher reading than the healthy tissue throughout the measurement period for the higher dose 0.2 mL case. Also evident in the figures is the fact that the readings for the healthy tissue are approximately constant over the four days of measurement, but the readings from the tumor show a peak on day 14 after injection of the cancer cells in FIG. 8A and on day 15 in FIG. 8B.

The results from in vivo animal model experiments presented above demonstrate that embodiments may be used as an intraoperative tool (e.g., a hand-held probe, a robotically controlled probe, etc.) for distinguishing between cancerous and healthy tissue in an animal. The embodied method and system presented above may be useful in accurately assessing surgical margins. An exemplary probe can differentiate between cancerous and noncancerous tissue without the use of conjugated $Fe_2O_3$ NPs. However, in alternative embodiments, the use of a MAbs-NP conjugate in a detection scheme may be attractive for enhancing the sensitivity of the measurement. The use of MAbs-NP conjugates is also attractive because of the potential to use the NPs in treatment of the cancer by hyperthermia after they have been used in its detection. Hyperthermia treatments involving NPs heated using EM waves may offer a targeted treatment for certain forms of cancer. Metallic NPs can also be used to enhance radiation therapy, so that the technique presented here addresses both intraoperative cancer detection and treatment of surgically non-resectable diseased tissue.

Ex Vivo Experiments on Excised Tissue from Cancer Surgeries

In addition to measurements on animal models, an exemplary embodiment's performance was also evaluated in the presence of human tissue such as would be encountered during cancer surgery. Measurements were recorded on tissues excised from cancer patients that were part of a pilot study evaluating a combined approach to resective cancer surgery involving preoperative PET/CT imaging of the patient, intraoperative hand-held gamma probe detection, PET/CT imaging of the excised tissue specimens, and postoperative PET/CT imaging of the patient. As part of the procedure for the study, a combined PET/CT analysis was performed on each tissue sample before it was subjected to probe readings, so that probe readings were made with some idea of which samples contained cancer and where it was located.

Tissue samples were analyzed from four surgeries, performed on patients with four different types of cancer. Before each set of measurements, both the plexiglass stage and the probe head were covered with plastic wrap to avoid bio-contamination. This did not affect the probe readings. The procedure for measurements on excised human tissue was virtually identical to that for the xenograft mouse models. The probe was oriented at an angle 20° from the vertical to assure as close to a pointwise measurement as possible. A similar procedure was used to that described for xenograft mice. The driving signal was a 7 Vpp, 99 kHz sawtooth waveform.

Figure 9:
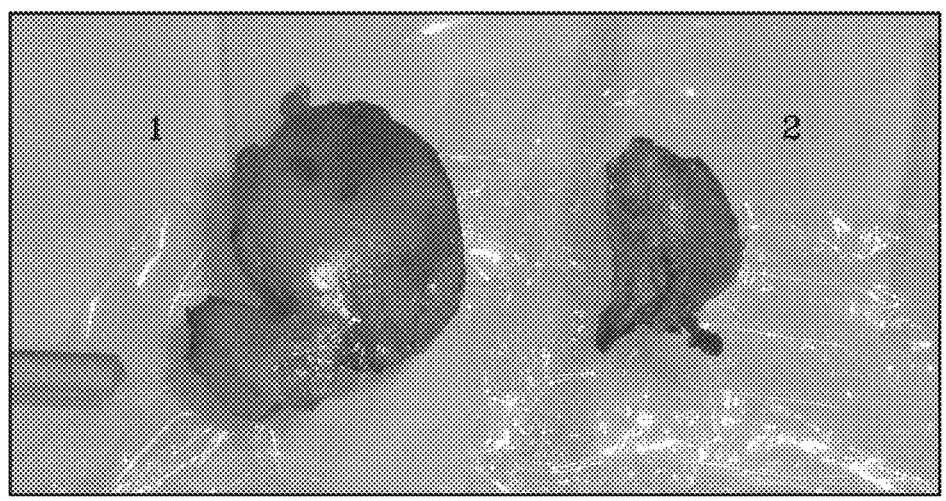
FIG. 9 shows tissue samples excised during human lymphoma surgery, consisting of a diseased lymph node and a sample of healthy tissue removed from the same vicinity.

Tissue samples from four different cancer surgeries were obtained and analyzed. The first tissue sample was from a lymphoma case. A diseased lymph node and a sample of healthy tissue from its vicinity were studied as seen in FIG. 9. Three measurements were performed on each, with the probe moved between tissue samples after each measurement. Therefore, repeatability on a given location could only be guaranteed to within millimeters.

Figure 10:
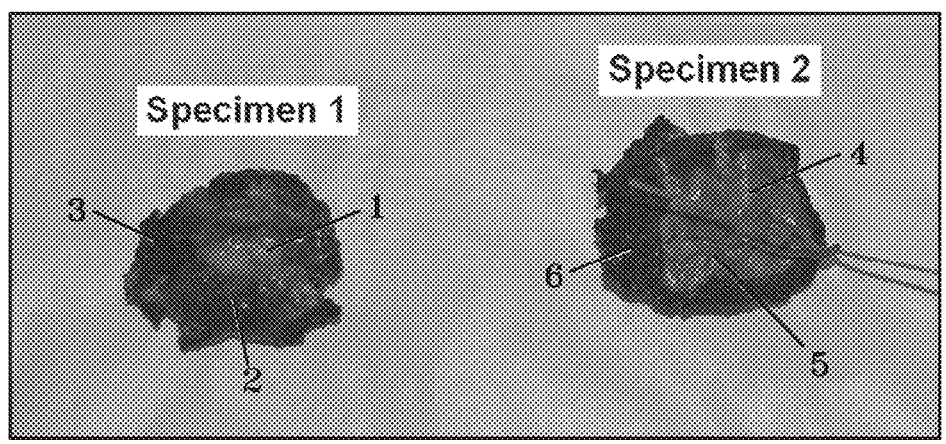
FIG. 10 shows tissue samples excised during a human hepatic cancer surgery, where probe measurements were performed at six different locations, including the tumor, healthy tissue near the tumor, cauterized tissue on specimen 1, healthy tissue, and cauterized tissue on specimen 2.

The next set of tissue specimens was from a liver cancer. The liver tumor was a recurrent breast cancer that had metastasized to the liver. Two segments of liver tissue were obtained and are shown in FIG. 10. Specimen 1 contained a tumor surrounded by a margin of healthy liver tissue, and specimen 2 was determined to be free of cancer by micro PET/CT scan. Both samples had cauterized edges, which can be clearly seen in FIG. 10. Probe measurements were performed at six locations total, or three on each sample. Measurements were taken on the tumor, the healthy tissue and the cauterized edge on specimen 1. Measurements were taken on the cauterized edge and on two locations within the healthy tissue of specimen 2. All six locations are designated on FIG. 10.

In the third case, probe measurements were performed on a sample of metastatic ovarian signet ring cell cancer that had metastasized to the abdominal wall, omentum and small intestine. Measurements were made on a piece of tissue excised from the omentum. A PET/CT image representing a subsurface slice of the same tissue sample appears in FIG. 11. Three tumors were discovered by palpation during surgery, including one just below the surface of the sample and two embedded tumors. Measurements were taken at four locations, indicated in FIG. 11. These include a region of healthy tissue (1), the tumor just below the surface (2) and the embedded tumors (3,4).

Figure 12A:
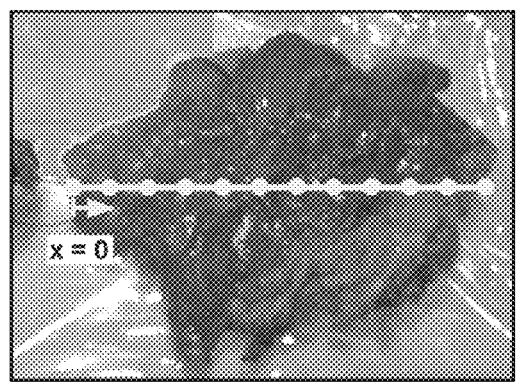
FIGS. 12A and 12B, respectively, show a photograph of tissue sample from human colon cancer metastasized to the distal psoas muscle showing the locations of probe readings that were taken in the x-direction along 6.3 mm intervals, and a PET/CT image showing the location of the main tumor mass, where the probe scan did not pass through the main tumor, but it did pass over an interior tumor embedded in the tissue sample.
Figure 12B:
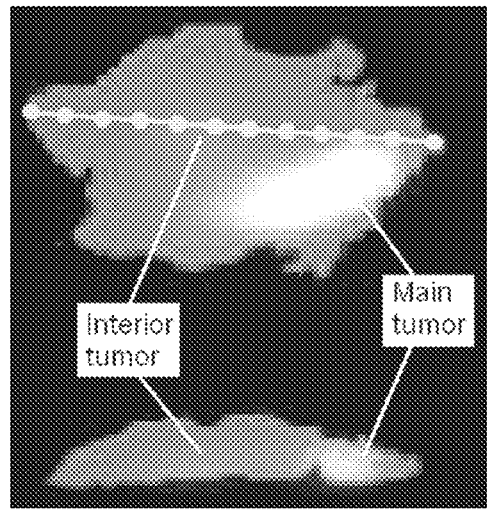

Finally, a series of probe measurements were taken on tissue excised from the distal psoas muscle from a metastatic colon cancer case. Measurements were taken along a straight line spaced at 6.3 mm intervals in an attempt to form an image of the varying EM properties along the top edge of a "slice" of the tissue sample. This was done without prior knowledge of where the cancerous tissue was. A datum was chosen at one end of the sample and set to x=0. The y-axis was held constant, but the plexiglass stage was moved 6.3 mm in the x-direction after every probe reading. With each new reading, the z-axis was re-zeroed so that the probe always came to rest just on the surface of the tissue during the measurement. A photograph of the tissue sample is shown annotated with the locations of the probe readings in FIG. 12A. PET/CT images of the tissue sample showing the locations of disease are shown alongside in FIG. 12B. Note that the probe scan did not traverse over the main mass of the tumor, but did travel over an embedded tumor in the interior of the tissue sample and by the edge of the main tumor mass.

Figure 13:
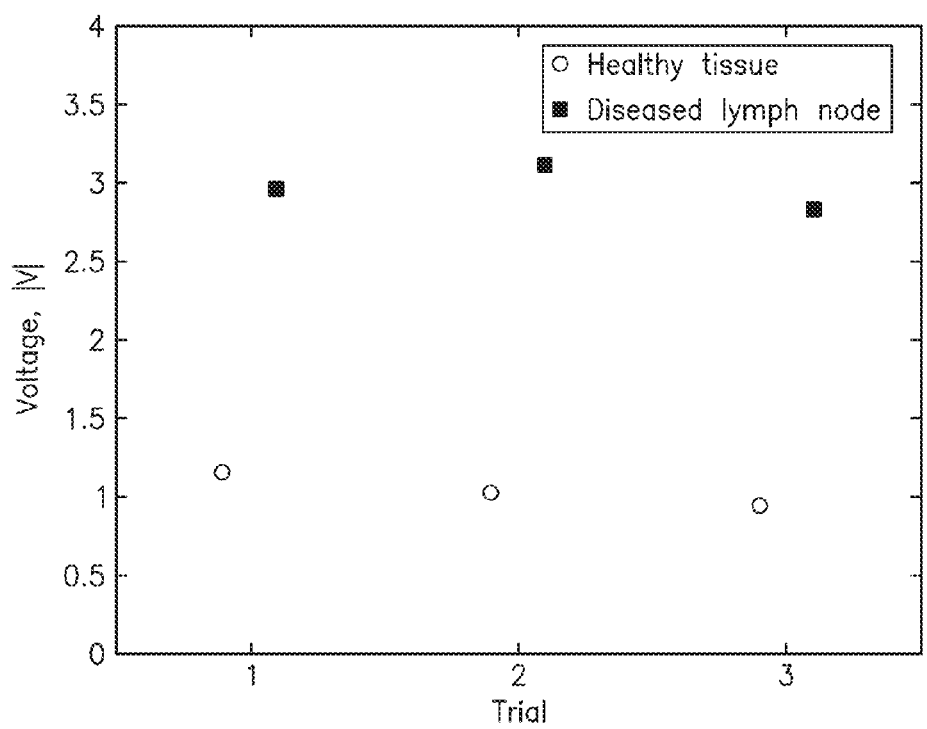
FIG. 13 shows typical detector voltages recorded by the EM probe at a fixed phase for three separate measurements each on a diseased lymph node and healthy tissue removed from the same vicinity during human lymphoma surgery (see FIG. 9), where the error bars are smaller than the data markers and are not shown, and the readings on the diseased lymph node have a mean value of 2.97 V and a standard deviation 0.15 V, while readings on the healthy tissue have a mean value of 1.03 V and a standard deviation 0.10 V.

Results of probe measurements on tissue excised during surgery from a lymphoma case (see photo in FIG. 9) are presented in FIG. 13. Three readings each were performed on the diseased lymph node and on the sample of healthy tissue removed from its vicinity. The error bars are smaller than the data markers and are not shown in the figure. Note the significant difference in voltage drop between cancerous and healthy tissue, and the repeatability of the measurements. Readings on the diseased lymph node have a mean value of 2.97 V and a standard deviation 0.15 V, while readings on the healthy tissue have a mean value of 1.03 V and a standard deviation 0.10 V. It is interesting to note that the diseased lymph node gives a larger voltage drop than the sample of healthy tissue, whereas the tumor in the xenograft models showed a smaller voltage drop compared to the healthy tissue. It is important to stress that it is not the absolute value of the probe readings that is important but rather that there is a difference in voltages between the two tissues.

A photograph of the two tissue specimens excised during surgery for a hepatic cancer with the measurement sites marked is provided in FIG. 10. One measurement consisting of three probe readings was performed on each site. The mean and standard deviation for the probe readings at each site are listed in Table 1:

TABLE 1

| Site | Description | Mean voltage, \|V\| | σ, \|V\| |
|---|---|---|---|
| 1 | Tumor | 2.93 | 0.30 |
| 2 | Healthy tissue near tumor | 4.79 | 0.32 |
| 3 | Cauterized tissue | 1.14 | 0.04 |
| 4 | Healthy tissue | 8.75 | 0.06 |
| 5 | Healthy tissue | 7.71 | 0.18 |
| 6 | Cauterized tissue | 0.86 | 0.03 |

Again, a significant difference is registered between the voltages (at a fixed phase) on the tumor and those on healthy tissue, in this case with healthy tissue giving significantly larger voltage drops than tumor. The two readings on cauterized tissue display readings lower than either healthy tissue or tumor, possibly indicating poor mobility of the charges that lead to eddy currents in this type of tissue. It is interesting to note that the readings on site 2, which is an area of healthy tissue in the vicinity of the tumor on specimen 1, gives a probe reading (4.79 V) that is between the readings on the tumor (2.93 V) and the healthy tissue on specimen 2 (7.71-8.75 V). This occurred because as the probe was pushed into that location, the surrounding tissue containing the tumor wrapped itself around the probe tip. Since the tumor site was sufficiently close to site 2, the recorded voltages from site 2 are between those of the values obtained on the tumor and the cancer-free region.

Figure 11:
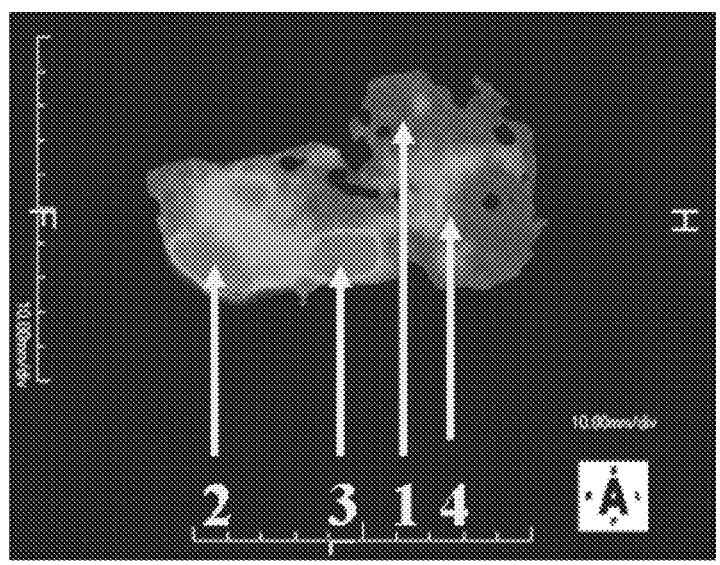
FIG. 11 shows a subsurface PET/CT image of the sample of human metastatic ovarian signet ring cell cancer from the omentum showing locations where measurements were taken with the EM probe, with the measurements taken on healthy tissue, a tumor just below the surface of the sample, and tumors embedded below the surface.
Figure 14:
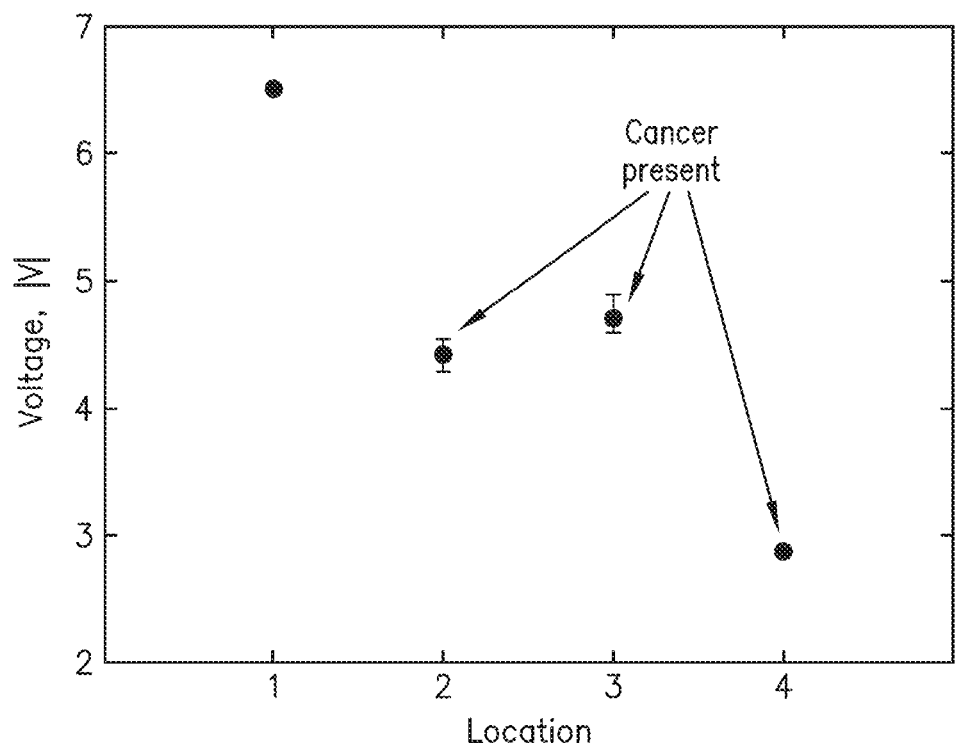
FIG. 14 shows results of probe readings on a sample of human metastatic ovarian signet ring cell colon cancer (see FIG. 11) at four different locations, where the tumor is just below the surface and the two embedded tumors show probe readings that are well below the reading on healthy tissue.

The subsurface PET/CT scan of a sample of signet ring cell colon cancer with measurement sites marked is provided in FIG. 11. One measurement consisting of three probe readings was performed on each site. These include a region of healthy tissue (1), the tumor just below the surface (2) and the embedded tumors (3,4). The results of the probe measurements are presented in FIG. 14. Notice that the voltage reading for the healthy tissue in region (1) is significantly higher (6.51 V) than any of the other readings. The surface tumor from region (2) gives a probe signal of 4.41 V, while the embedded tumors at sites (3) and (4) give readings of 4.70 V and 2.86 V, respectively. Again, the probe is able to distinguish between tissue containing disease and healthy tissue.

Figure 15:
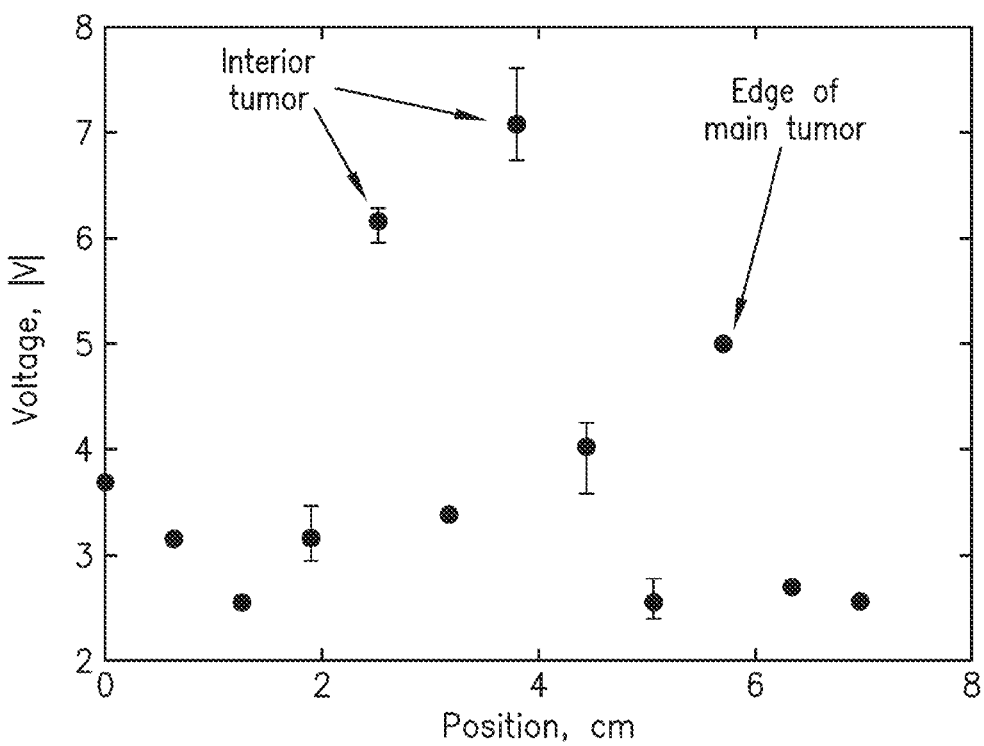
FIG. 15 shows results of probe readings on colon cancer metastasized to distal psoas muscle at locations shown in FIG. 12, where readings at 2.54 and 3.81 cm correspond to the embedded interior tumor that is visible on the PET/CT image, the line of measurement does not actually go through the main tumor mass, but the location at 5.72 cm corresponds to tissue just at the top edge of the main tumor, and this location does show an elevated reading.

A PET/CT image of a section of distal psoas muscle, the site of metastasized colon cancer, is shown in FIG. 12. In this case, the probe was spot-rastered along a straight line without prior knowledge of the exact location of the embedded tumor, taking one measurement consisting of three probe readings every 6.3 mm as indicated in FIG. 12. The average probe readings at each location along the line of measurement are shown in FIG. 15. Note that the readings at 2.54 and 3.81 cm correspond to the embedded interior tumor that is visible on the PET/CT image. The line of measurement does not actually go through the main tumor mass, but the location at 5.72 cm corresponds to tissue just at the top edge of the main tumor, and this location does show an elevated reading. The results presented in FIG. 15 show that the example probe would perform well as an intraoperative probe for detecting cancerous regions during surgery. Its utility as an imaging tool to generate a map of the EM properties of a piece of excised tissue, and thereby determine the probable location of disease either in-vivo or ex-vivo, is also apparent.

The results of the experiments on xenograft mice and excised human tissue clearly show that the prototype EM probe exhibits potential as an intraoperative device in that it consistently distinguishes between cancer and healthy tissue in the same vicinity. An intraoperative probe designed along the principles explored in this work could easily be nulled against healthy tissue of the type containing the cancer, and the remaining tissue could be scanned for presence of the disease.

Figure 16:
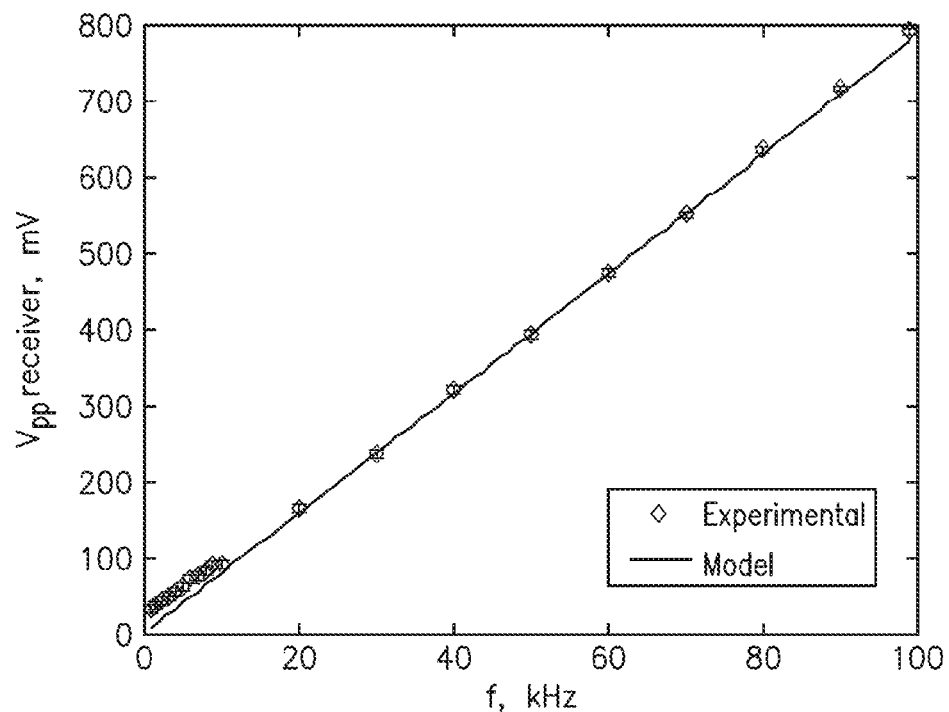
FIG. 16 shows peak-to-peak magnitude of receiver response as a function of driving frequency f for a single 7.39 mm loop of 18 gage copper wire, where the driver coil is driven by a 7 Vpp sinusoid.
Figure 17:
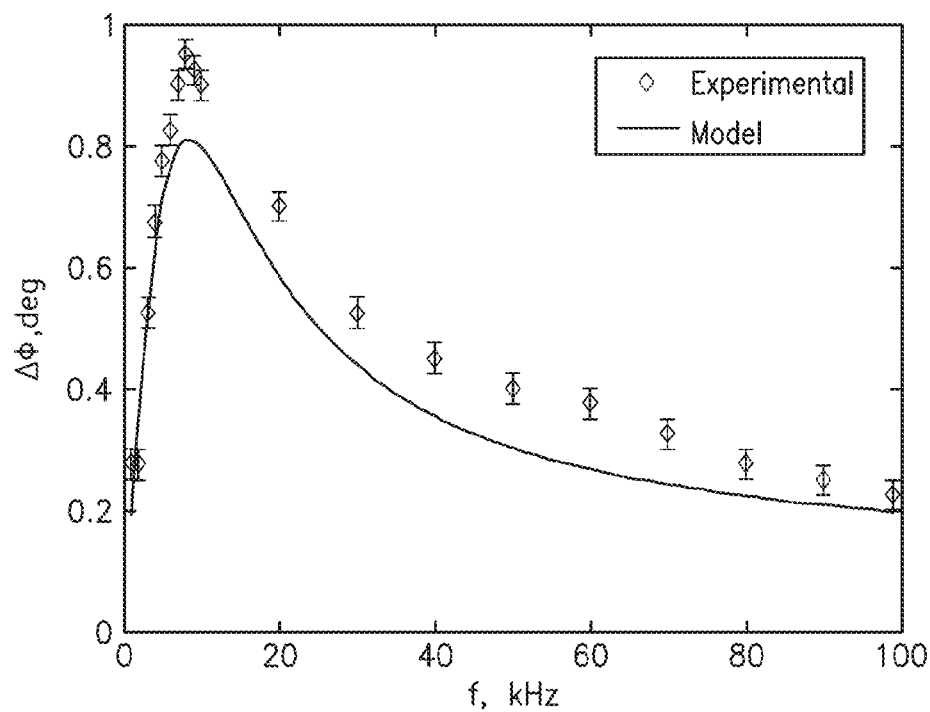
FIG. 17 shows phase difference $\Delta\phi$ between driver and receiver coils as a function of driving frequency f for a single 7.39 mm loop of 18 gage copper wire, where the driver coil is driven by a 7 Vpp sinusoid.

FIGS. 16 and 17 show the receiver voltage and phase response, respectively, of the probe to a single 7.39 mm copper wire loop when driven by 7 Vpp sinusoids of varying frequency. Both the model and the experimental data show a peak in the phase response at a driving frequency of 8 kHz. Although the magnitude response decreases at lower frequencies, phase response is even more sensitive at lower frequencies. This was also evident in data comparing the probe response to single, concentric copper wire loops of different diameters with a 99 kHz driving frequency to the response with a 50 kHz driving frequency (not shown). An intraoperative device designed to take advantage of eddy current detection may therefore operate at a frequency even lower than 99 kHz to take advantage of large phase shifts (e.g., 60 Hz).

As discussed above, the choice of waveform may have a significant effect on the voltage reading of an exemplary embdiment. A sawtooth driving signal yields a larger voltage reading than a sinusoidal driving signal. Indeed, when a sinusoidal driving signal is used, the change in voltage in the receiver coil of the probe in the presence of tissue specimens may be too small to read. Because sinusoidal excitation does not produce a measurable probe response in tissue, the effect of waveform on receiver voltage was explored using wire loops.

Figure 18:
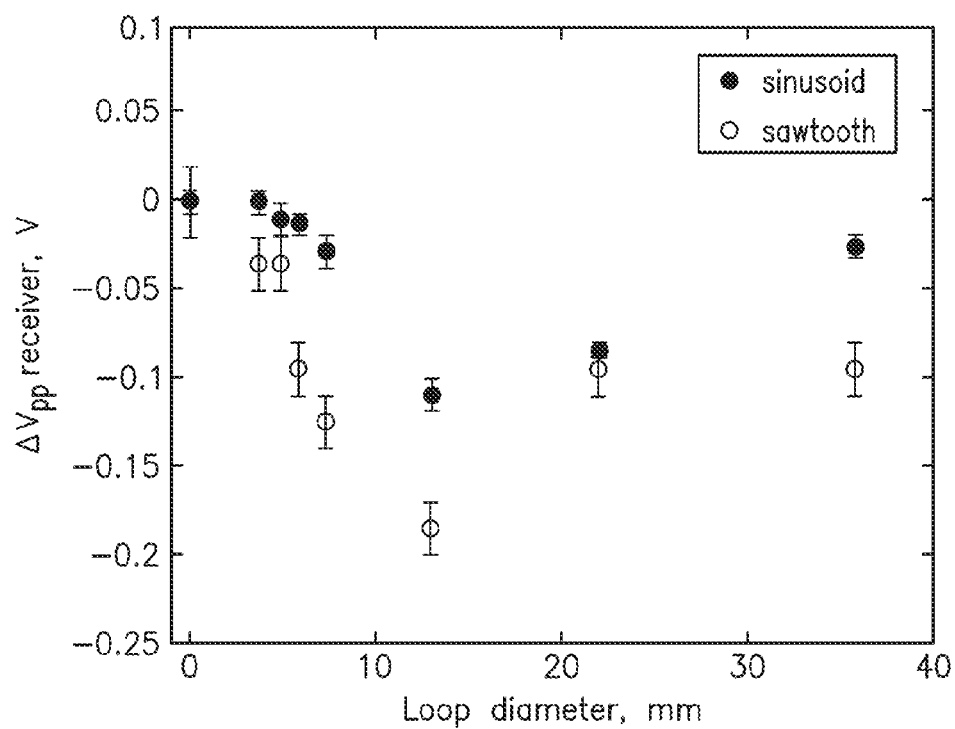
FIG. 18 shows peak-to-peak voltage of receiver coil for experiments on single concentric loops of 18 gage copper wire of varying diameter, where the driving signals are a sawtooth or sinusoid of 7 Vpp and 99 kHz.
Figure 19:
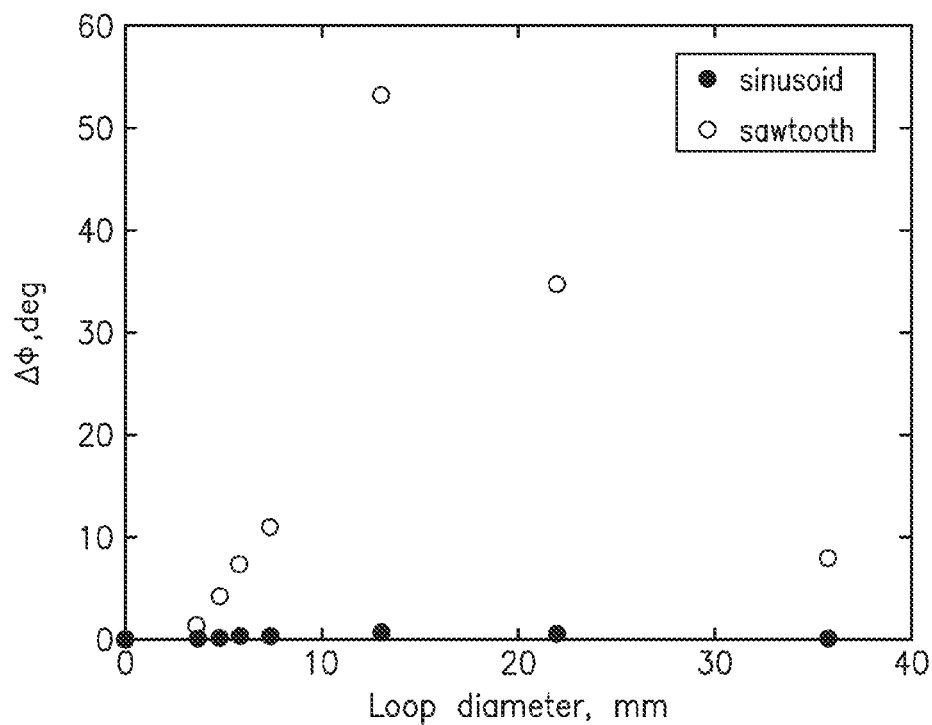
FIG. 19 shows the phase shift of probe for experiments on single concentric loops of 18 gage copper wire of varying diameter, where the driving signals are a sawtooth or sinusoid of 7 Vpp and 99 kHz and the error bars are smaller than the data markers.
Figure 20:
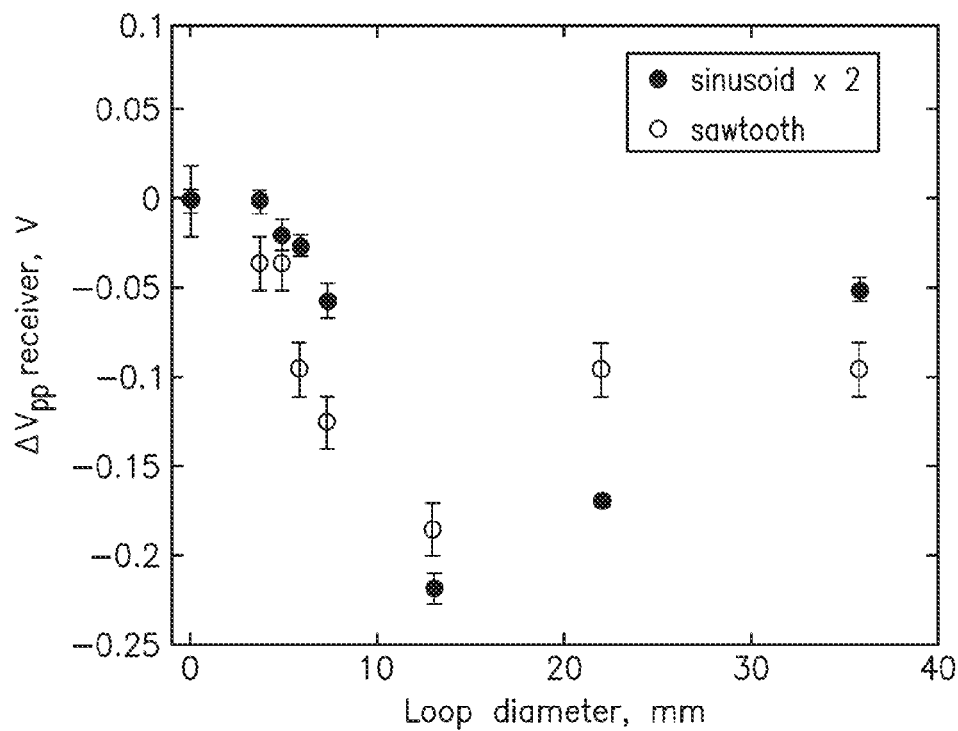
FIG. 20 shows peak-to-peak receiver voltage (Vpp) of receiver coil for experiments on single concentric loops of 18 gage copper wire of varying diameter, where the driving signals are a sawtooth or sinusoid of 7 Vpp and 99 kHz, and the results for the sinusoidal driving signal have been multiplied by a factor of 2 to show that they have the same qualitative dependence of the peak-to-peak receiver voltage versus loop diameter.
Figure 21:
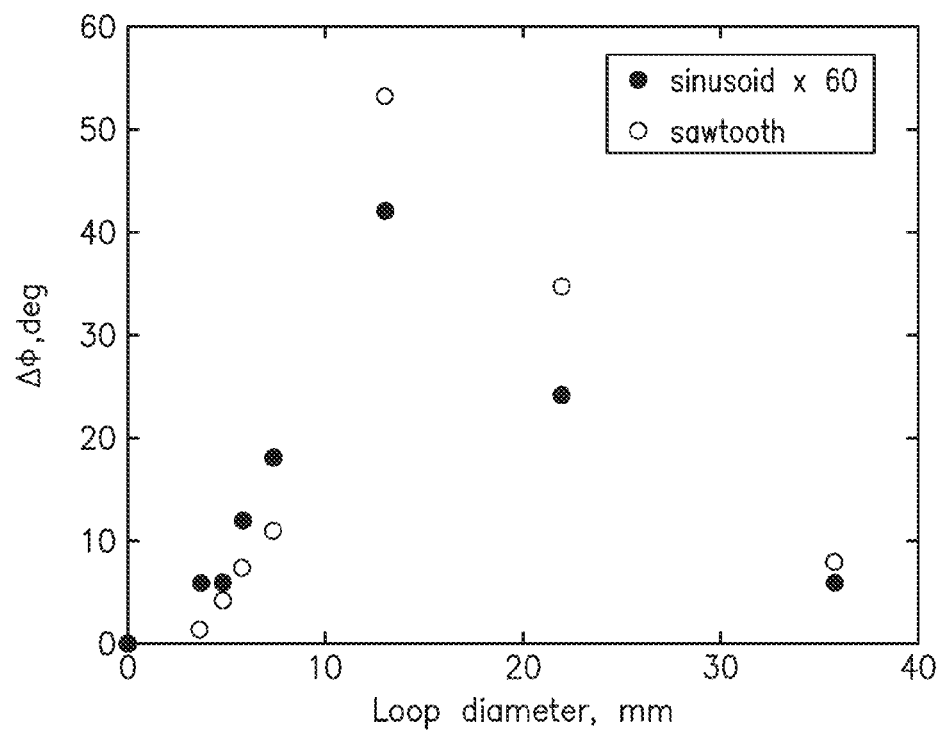
FIG. 21 shows the phase response of probe for experiments on single concentric loops of 18 gage copper wire of varying diameter, where the driving signals are a sawtooth or sinusoid of 7 Vpp and 99 kHz, the results for the sinusoidal driving signal have been multiplied by a factor of 60 to show that they have the same qualitative dependence of the peak-to-peak receiver voltage versus loop diameter, and error bars are smaller than the data markers.

FIGS. 18 and 19 show the probe response to single, concentric 18 gauge copper loops of varying diameter for both 7 Vpp, 99 kHz sinusoid and sawtooth driving signals. FIG. 18 shows the receiver voltage and FIG. 19 shows the phase shift. Because the null receiver voltages are very different for the two waveforms (approximately 830 mV for the sinusoid and 4.8 V for the sawtooth), the receiver voltages are shown relative to the null point. Note that the difference in receiver voltage between the sawtooth and sinusoid cases is not great (FIG. 18), whereas the difference in phase shift is substantial (FIG. 19). FIGS. 20 and 21 demonstrate more clearly the effects of the different waveforms on both receiver voltage and phase. In FIG. 20, the receiver voltage for the case with the sinusoidal driving signal has been multiplied by constant scaling factor of 2 to bring it to the level of the receiver voltage for a sawtooth driving signal. FIG. 21 shows that a scaling factor of 60 is required to bring the phase shift for the sinusoidal case to the level of the phase shift for the sawtooth case. In both cases, it can be seen that regardless of the waveform used, the qualitative shape of the voltages versus loop diameter is the same.

The operation of the lock-in amplifier that was used to collect the phase shift data was described above. In particular, the lock-in amplifier works by multiplying the incoming signal from the receiver coil by a sinusoid at a reference frequency, dictated by the signal from the driver coil. The particular models of lock-in amplifier used in the described validation studies (SR510 and SR530) are unable to lock in on any frequency greater than 100 kHz. Therefore, when the driver coil of the probe is driven by a 99 kHz sawtooth, one would expect the lock-in amplifier to measure the response of the 99 kHz harmonic of the receiver coil signal only. The remarkable phase shift between the receiver and driver coils for a sawtooth driving signal observed in FIGS. 19-21 cannot be explained by Fourier decomposition of the sawtooth signal and lock-in amplification alone.

Imaging Embodiments:

Having demonstrated that it is important to monitor phase as well as voltage, a device to raster the EM probe without affecting its functionality was developed for the purpose of imaging biological tissue extracted during cancer surgery. The raster device is composed of non-conducting parts, namely plastics, and it has been found to allow the probe to remain in contact with an unknown terrain.

Using an exemplary embodiment, images based upon the magnitude of the induced voltage in the receiver coil of the EM probe and the phase, were obtained for paraffin, rectangular, phantoms. In the disclosed embodiments, phase-based imaging is a more sensitive technique compared to imaging using voltage magnitudes.

The imaging of phantoms may be directly applied to surgically excised tissue samples. The EM probe's ability to detect small changes in the specimen's electromagnetic characteristics, as well as to reproduce the location of the variation of these changes with known uncertainties, will allow for the successful imaging of tissue. For instance, in the signet ring cell case, the probe detected variations in signal based on its proximity to cancer. In this case, it is believed that the EM probe can and will produce an image of the locations containing cancer. This will be an invaluable tool for surgeons in quantifying surgical margins and provide priceless peace of mind for patients and their families.

Accordingly, various embodiments include systems and methods for medical imaging using an EM probe. To demonstrate the capabilities of an exemplary embodiment, a passive design to allow the probe to traverse a sample or phantom was constructed. In various embodiments, the motion of the probe may be controlled either by a Velmex VP9000 Controller or by a MAXNC CL2 Milling Machine. The MAXNC stage is used for measurements of the surgically excised tissue and the rectangular phantoms, while the Velmex stage is used to measurements on the round phantoms and the wire loops. The Velmex VP9000 Controller uses the Velmex VP9000 Series Controller Ver. 99.1.B software. The stages utilized are Unislide® by Velmex, Inc, 6 in wide, 5 in travel stages. The x-axis is a MB6012K1J-S8 stage and the z-axis is a MA6012K1-S8-0. Whereas the MAXNC CL2 is a self contained 4-axis system controlled using MAXNC system software in a DOS computing environment on a Gateway 2000 P5-90 Pentium computer. For the purposes of this design setup, the fourth axis, the rotational axis, is unnecessary and hence it is removed. See FIG. 4 for a dimensioned representation of the MAXNC setup without the rotational axis.

Despite the ability to move the probe, various embodiments also include a means to allow the probe to traverse an unknown terrain without damaging the probe, altering its output signal, or damaging the sample, while still maintaining knowledge of the probe tip location. So as not to affect the output signal of the receiver coil, there should be no bulk metal parts near the probe. If there is bulk metal in the proximity of the probe the eddy currents that build in the metal will induce a proportionally larger current in the receiver than the sample, possibly swamping out the information about the sample. Exemplary embodiments use materials that do not support the formation of these eddy currents, such as plastic.

Figure 22:
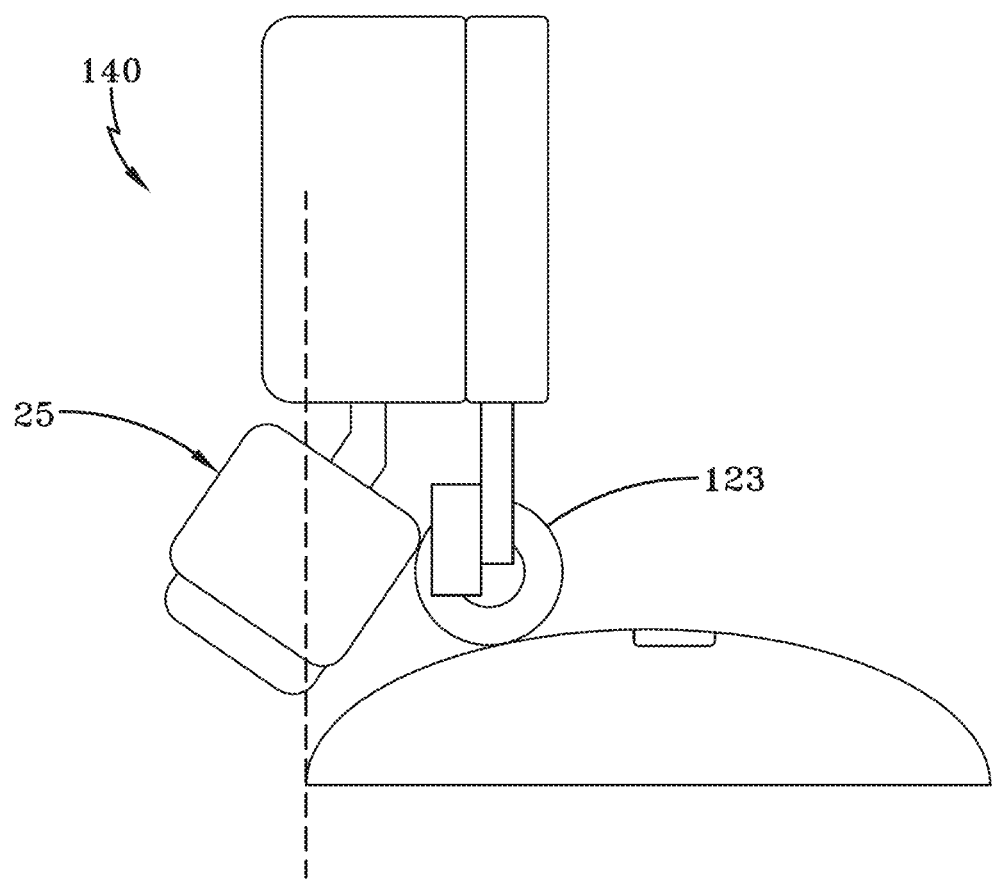
FIG. 22 is a schematic demonstrating the operation of an embodiment with the probe mounted on a raster device on a round phantom.

A raster device 140 was constructed for imaging using an EM probe 25. A schematic of that embodiment is shown in FIG. 22. In the embodiment shown, the probe 25 is disposed at an angle (e.g., 20°) with respect to the sample in order to minimize contact area with the sample. Doing this yields a more point-wise measurement, increasing spatial accuracy. As shown in FIG. 22, the imaging arrangement of an exemplary embodiment is capable of traversing an unknown, yet gently sloping terrain. In the case of certain tissues and tissue specimens, the terrain is also soft, so it is useful to have wheels 123 in order to keep the probe from experiencing a large lateral force. Wheels 123 were modified by cutting the connective center piece so the wheels could be inverted close to each other when mounted on the device.

(a) Preparation of Phantoms

Figure 23:
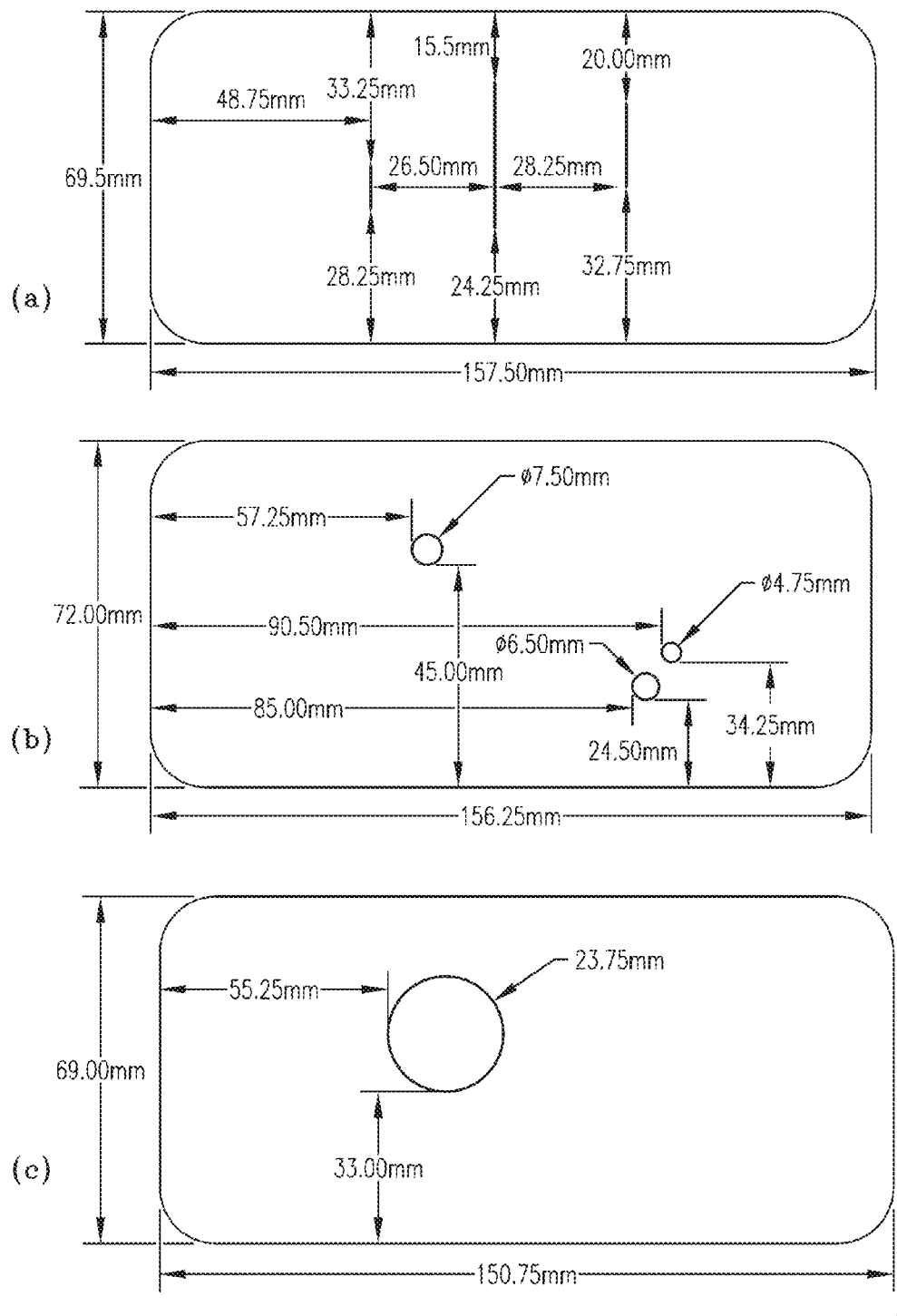
FIG. 23 is a schematic of various rectangular paraffin phantoms used to test various embodiments.

Several phantom specimens were constructed to simulate or mimic some characteristics of real tissues. These phantoms provided varied features with a known configuration in order to assess the specificity and sensitivity of the raster device that uses the exemplary EM probe. Various phantoms constructed using a combination of paraffin wax and 18 AWG bare copper wire are illustrated in FIGS. 23 (a)-(c).

(b) Imaging the Phantoms

Figure 24:
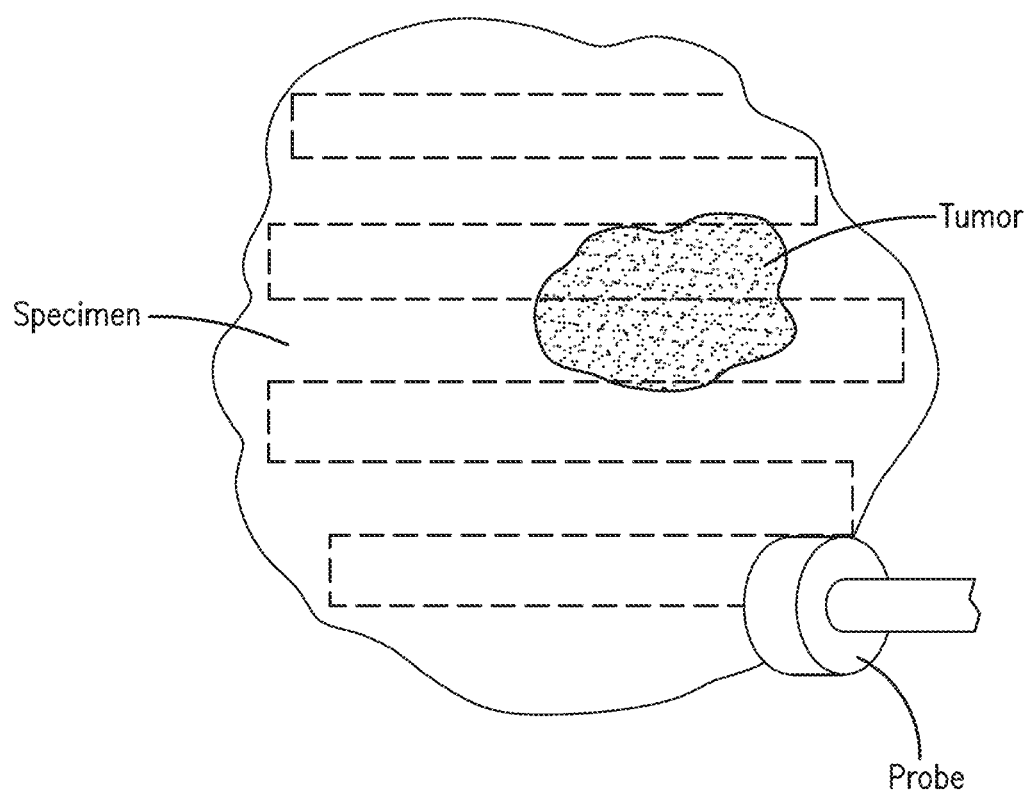
FIG. 24 is a schematic demonstrating an imaging embodiment where the EM probe may be rastered over the specimen.

In an exemplary embodiment, the EM probe can be rastered over the specimen to create an image showing location of diseased tissues, as seen in FIG. 24. In the simulation, measurements of amplitude and phase shift by an exemplary EM probe were made by raster scanning the probe across a phantom in order to create an image. In this case, the probe's motion is controlled by the MAXNC stage for the rectangular phantoms and the Velmex stage for the round phantoms. The raster device is attached to the probe. As depicted in FIG. 22, the probe's tip may be placed at an angle of approximately 20° from the vertical. For the validation experiments described below, the driving function is a 7 Vpp, 99 kHz, Sawtooth, and the scope is set to 200 mV/div for the phase output, 100 mV/div for the magnitude output, and 5 sec/div.

The purpose of the phantom experiments was to demonstrate that an exemplary embodiment may be used as an imaging device. Accordingly, the phantom is taped off with electrical tape to ensure a repeatable origin and to set the axes of the image. Next, the probe tip, i.e. the part of the probe angled towards the phantom surface, is centered on the origin of the phantom. The z-axis is brought down close enough to the phantom to partially depress the syringe/mini spring assembly. Also, care should be taken that the wheels are making even contact with the phantom surface, so that they will roll evenly across the phantom.

Once the probe is in place, the stage is zeroed such that this is the defined origin. Now, using the "Rel" keys on the lock-in amplifier, both the magnitude, R, and the phase, $\phi$, are zeroed. The offset of the magnitude, $R_{offset}$, and the reference phase, $\theta_{ref}$, are recorded. The stage is then programmed to move 87.5 mm in the x direction, at a rate of 2.08 mm/s. In the case of the MAXNC, the uncertainty of the location of the probe tip is approximately 2 mm, since the rate is a parameterized function that must be tuned by stopwatch, and therefore has a human error uncertainty of about 1 second.

At the same time the stage begins to move, the oscilloscope begins a single line sweep. When this sweep is completed, the voltage information pertaining to phase and magnitude is collected and saved on a PC as a text file by using an RS-232 cable and the Agilent Scope Control Application software. The exemplary probe is then brought to its zero location along the x-axis and is stepped along the y-axis in increments of 2.5 mm. Again, the Rel keys are used to zero the magnitude and phase, and the process is repeated until the probe has stepped the width of the phantom in the y-direction.

Once this data is collected, it is processed in MATLAB 7.1 and 3-D surface plots are generated. Each of these plots is interpolated linearly between data points. The data then can be compared to the known dimensions of the phantoms.

For the round phantoms, a single scan through the center of the phantom is performed. This is similar to a single sweep of the rectangular phantom. In the case of the round phantoms, the probe is set up as previously shown in FIG. 22.

In order to accurately determine the position of embedded objects within the phantoms, or simulated tumors, the projection of what the EM probe "sees" must be estimated. Although the probe is set at a 20 degree angle from the vertical to ensure a single point of contact with the specimen at any time, the magnetic field lines extend into the surface of the specimen and thus, interact with it by inducing eddy currents at different depths. It is assumed that the distance between the edge of the EM probe tilted upward and the specimen is sufficiently large that the magnetic field lines cannot reach beyond the back edge of the probe. With this assumption, simple geometry gives the effective diameter of the probe as 12.5 mm, versus the 13.3 mm of the actual diameter of the probe.

Imaging with the EM probe may be necessary for applications to postoperative detection. If the surgeon can have more information about the success of the surgery before it is over, then more surgeries will be successful and more lives could be saved. To demonstrate the EM probe's ability to image, a set of three different rectangular phantoms were used.

Figure 25:
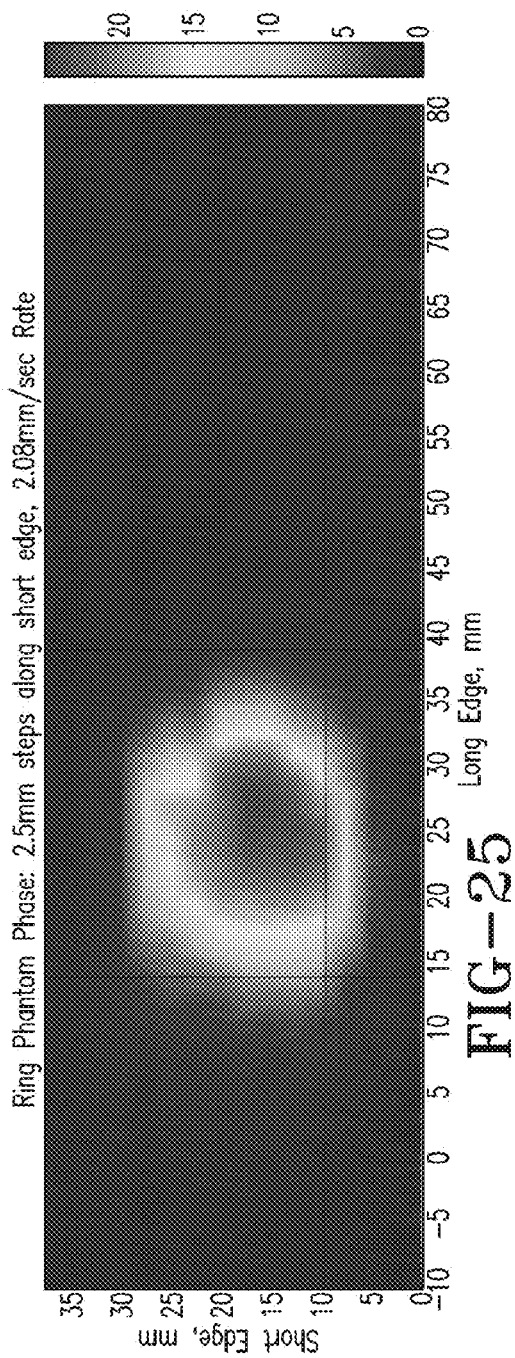
FIG. 25 is an image generated using the measured phase output on the rectangular, paraffin phantom with one embedded larger copper loop. Step size along the short edge is 2.5 mm. The phantom was scanned along the long edge at a rate of 2.08 mm/sec.
Figure 26:
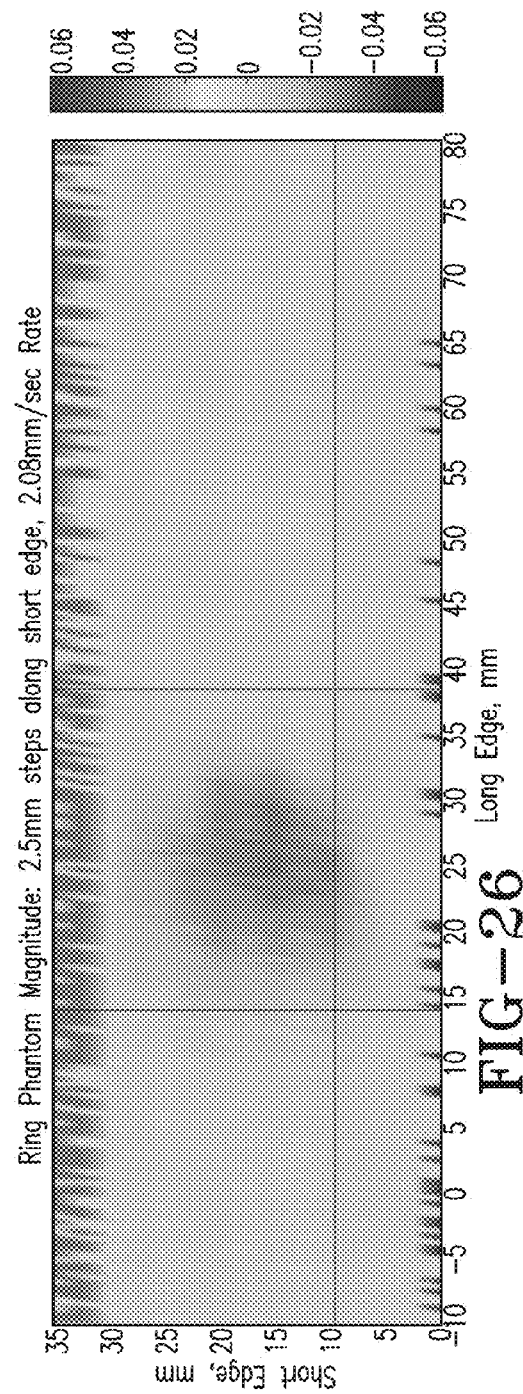
FIG. 26 is an image generated using the measured voltage magnitude output on the rectangular, paraffin phantom with one larger copper loop, the step size along the short edge being is 2.5 mm, where the phantom was scanned along the long edge at a rate of 2.08 mm/sec.

Example results from the first phantom has a single large wire loop are shown in FIGS. 25 and 26. It should be noted that the error in position along the long axis of these images is ±2 mm. This is because there is a 1 sec uncertainty in the MAXNC feed rate, and the scanning rate is 2.08 mm/sec. This problem may be addressed by using a more precise stage, such as the Velmex system, but with a third stage added for the third degree of freedom. It can be seen from FIGS. 25 and 26 that the EM probe can resolve bodies larger than its diameter; however, the edges are less distinct than the center of the ring in both the phase and magnitude images. This is likely because the intensity of the magnetic field produced by the eddy currents in the loop is greatest at the center. This effect will be less apparent in the case of tissues, because there the eddy currents are not as restricted as they are in the case of the wire loop. Moreover, FIGS. 25 and 26 clearly establish that the phase information yields much less ambiguous images than the images constructed from the magnitude of the induced voltages in the receiver coil.

These results further emphasize the fact that phase changes more significantly with smaller changes in sample attributes, i.e. changes in eddy current size, or conductivity, compared to changes in the magnitude. Finally, the error in the detection of the ring along the vertical axis is explained by the coarseness of the scan along that axis, i.e. in increments of 2.5 mm. It is further explained by the diameter of the probe, which is 13.3 mm. If the probe is centered about the scanning line, then the probe can gather information from nearly 7 mm on either side of the probe. Those interactions, however, are quite weak, but within 2-3 mm, the information is likely to be conveyed. For instance, a scan with the probe centered at 7.5 mm can detect the edge of the ring, which is located at 10 mm.

Standing Wave Reflection (SWR) and Time Domain Reflection (TDR) in Phase Sensitive Cancer Detection Embodiments comprise alternative arrangements and methods for measuring the phase and phase-sensitive amplitude. In various embodiments, the Standing Wave Reflection Ratio (SWRR) method and/or the Time Domain Reflection (TDR) method may be utilized for measuring the phase and phase-sensitive amplitude. In various embodiments, only a single coil (similar to the driver or receiver coils previously described) may be necessary. The coil may be placed in contact with the biological specimen, and connected to instrumentation via a data transfer cable or a wireless connection (e.g., Bluetooth™). Accordingly, an example system may resemble a transmission network as signals are launched into the coil and the resulting interference between forward and reflected waves (resulting in a standing wave) or arrival times are recorded. SWRR is the ratio between the forward and reflected waves in the transmission network, as measured by the maximum and minimum amplitudes of the standing wave. Time Domain Reflection is a temporal measurement of the reflected wave in a transmission line.

Figure 27:
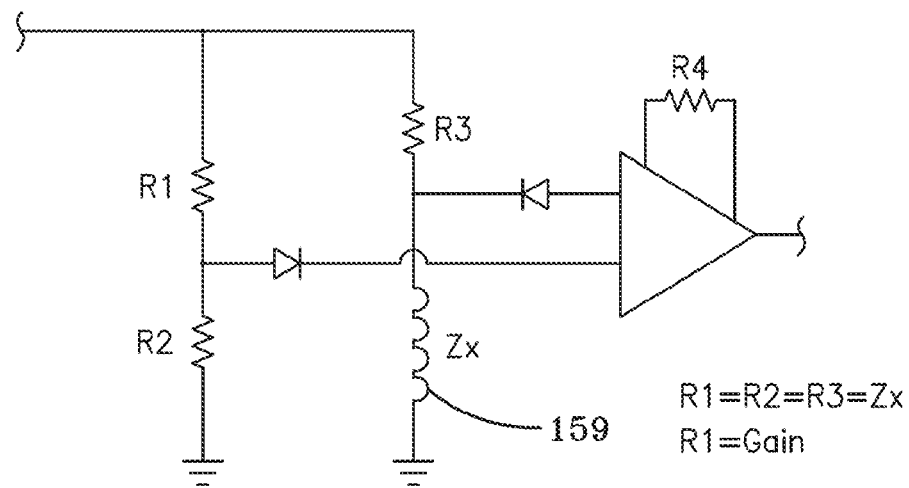
FIG. 27 is a schematic of an exemplary embodiment for SWR measurements.

In various embodiments, SWR measurements may be performed using a single coil. FIG. 27 shows a schematic of an exemplary system for SWR measurements. In various embodiments, the detection coil 159 acts as a tissue dependent impedance in a transmission network. Energy losses in the coil due to generation of eddy currents in the tissue cause a change in the inductive reactance of the detection coil. The interference between the incident wave and reflected wave results in a standing wave, which is directly affected in phase and magnitude by this change.

In various embodiments, the coil has been specifically designed to limit capacitive reactance and therefore is predominantly governed by inductive reactance. The capacitive reactance is further diminished by the low frequencies used in the detection coil. Embodiments may utilize an input frequency between 1 Hz and 1 MHz (e.g., 99 kHz), through coil 159. As designed, the phase shift is dependent on the resistive term and inductive reactance.

$$\mathrm{Tan}\phi = \frac{X_L}{R}.$$

A reference measurement of the SWR is taken in healthy tissue and summed with an adjustable voltage to achieve a null point. Any change in tissue properties may then be measured. Alternatively, the characteristics of the standing wave can be examined using Fast Fourier Transforms (FFTs), which can yield the phase shift with and without a biological specimen present.

Figure 28:
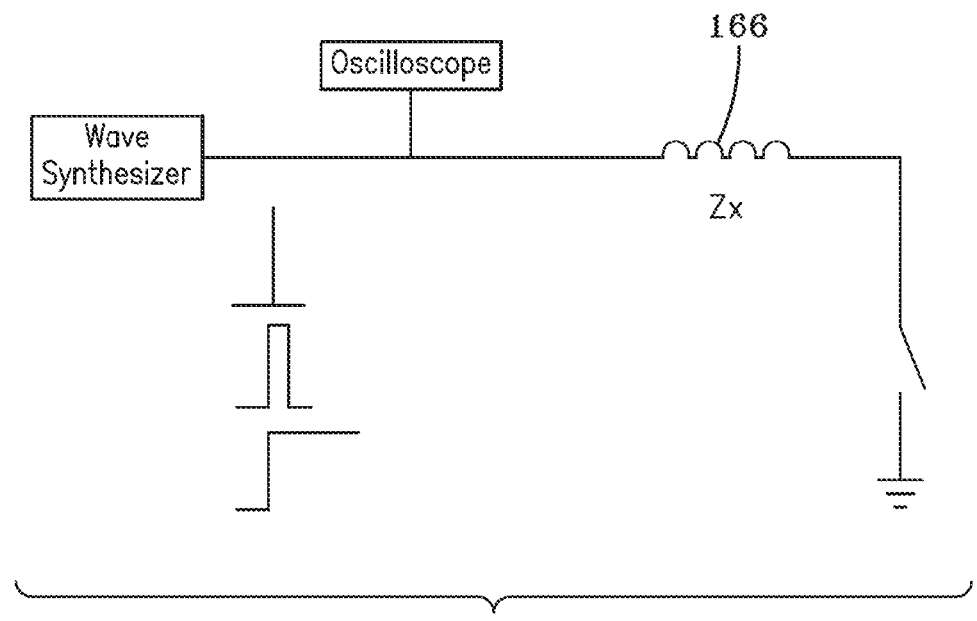
FIG. 28 is a schematic of an exemplary embodiment for TDR measurements.

In various embodiments, TDR may also be used with a single coil. With TDR, the detection coil is used in an open circuit configuration. FIG. 28 shows a schematic of an exemplary system for TDR measurements. A step input with a very rapid slew rate is applied to the detection coil 166. A finite time will elapse before the reflected wave is detected by the measurement device. This time signature is dependent on the detection coil's inductive reactance, which is sensitive to induced eddy currents within the tissue. A difference between healthy tissue and cancerous tissue is determined by the subsequent delay of the incident wave. The larger the eddy currents generated in the tissue by the step pulse the longer the delay.

Other Embodiments

A number of embodiments have been described. Nevertheless, it will be understood that various modifications may be made without departing from the spirit and scope of this disclosure. Embodiments are broadly applicable for numerous electromagnetic detection applications, for example, detection of minute quantities of metal in food. Accordingly, other embodiments are within the scope of the following claims.

Figure 29:
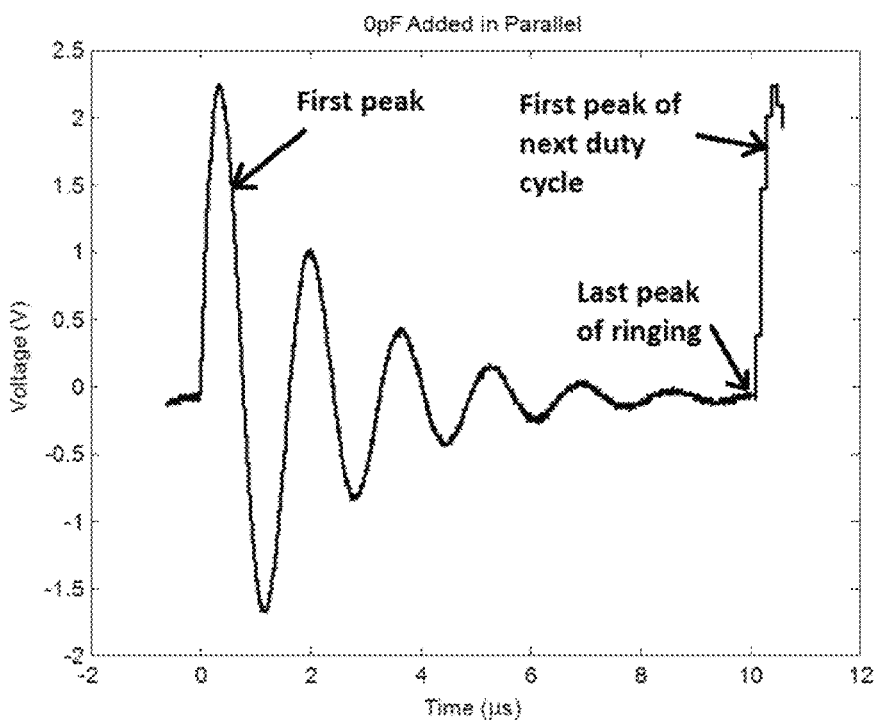
FIG. 29 is a graph illustrating the peaks of a duty cycle.
Figure 30:
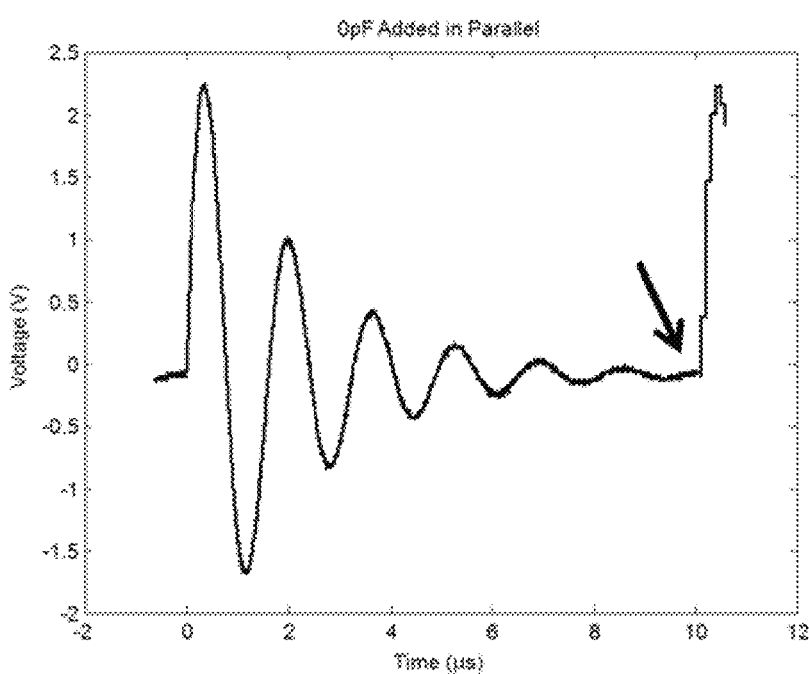
FIGS. 30-34 are graphs illustrating the intersection between the last peak and the first peak of the next duty cycle occurring on the sloping side of the last peak.
Figure 31:
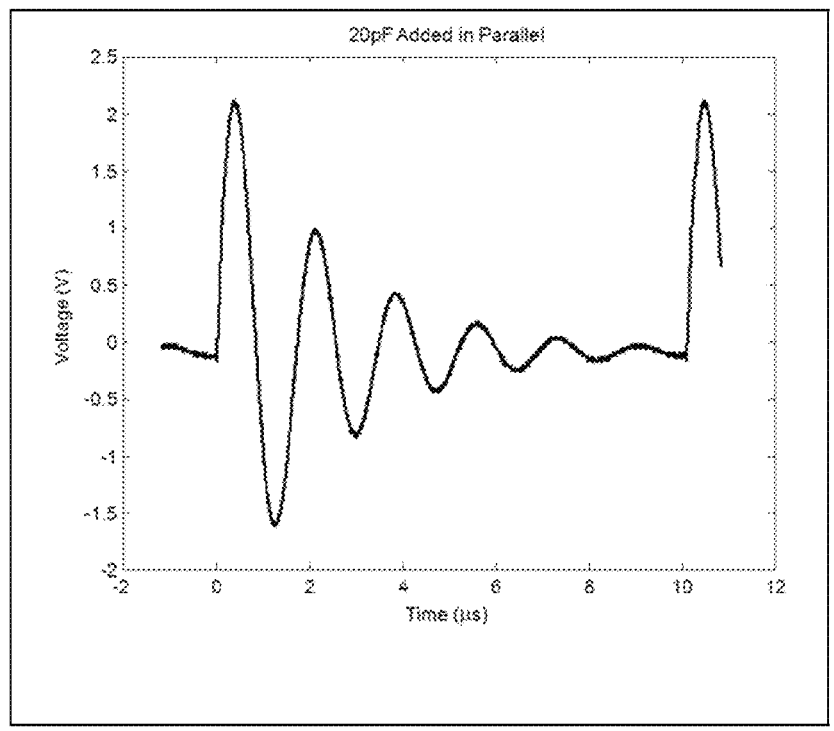
Figure 32:
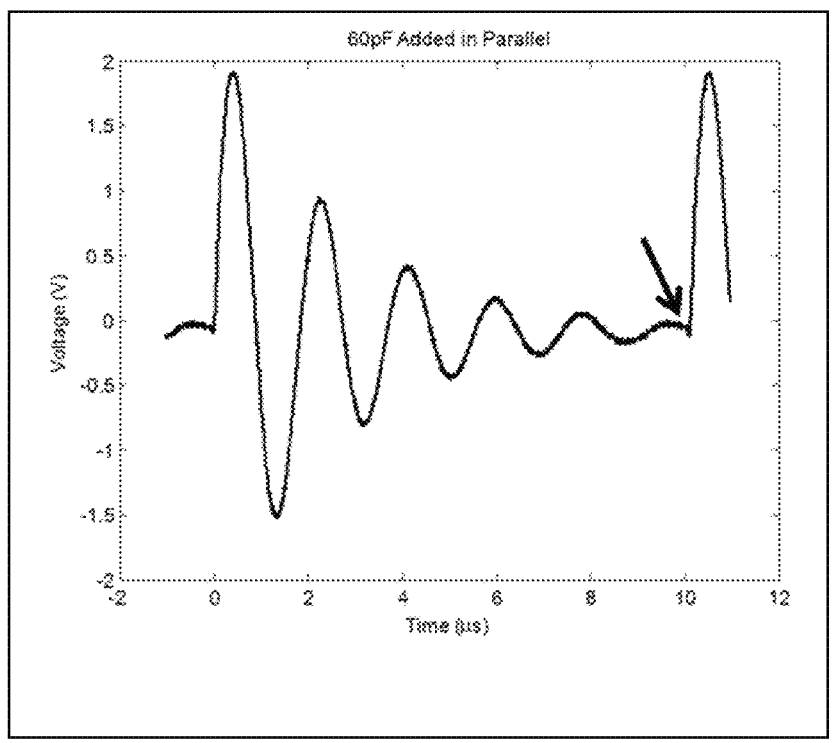
Figure 33:
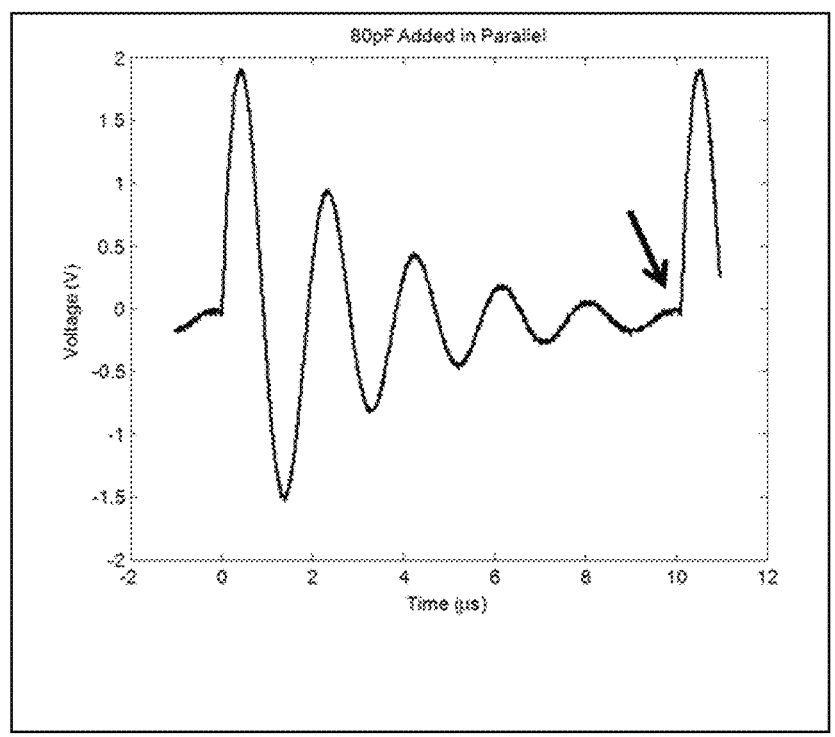

As discussed, the probe consists of a primary coil and secondary detector coil, inductively coupled by virtue of a time varying current applied to the primary coil. This results in a periodic detector coil voltage trace comprising several peaks. The occurrence of the peaks is referred to as "ringing." The fabrication of the coil is preferably designed such that the observed ringing (see FIG. 29 below) produces the largest number of peaks. If attention is paid to scale the coil inductance L, coil capacitance C, and coil resistance R in such a way as to preserve the LC and RC time constants then the dimensions of a probe can be changed (i.e. made smaller or bigger) while preserving its response as determined by the number of peaks in the ringing signal.

Capacitors may be added to an external circuit to maintain the products, LC and RC. Furthermore, if you have a probe with certain properties $L_p$, $R_p$, $C_p$, $L_d$, $R_d$, and $C_d$, then given a probe, say Probe A, with inductances $L_{pA}$ and $L_{dA}$, a second probe with similar detection characteristics (sensitivity) but different geometry and therefore different inductances $L_{pB}$ and $L_{dB}$, can be constructed if $L_{pA}C_{pA}=L_{pB}C_{pB}$ and $R_{pA}C_{pA}=R_{pB}C_{pB}$. However it is also desirable to improve the sensitivity of a given probe by making alterations to the external circuit and to do this in such a manner as to distinguish between tissue types.

Accordingly, in one embodiment of the invention, the sensitivity of a given probe design is improved by making alterations to the external circuit by adding capacitances. There are factors that enable the probe be distinguish between different tissue types.

It is difficult to design and construct a probe with specified values of $L_p$, $R_p$, $C_p$, $L_d$, $R_d$, and $C_d$. The reason is that $C_p$ and $C_d$ are intra-winding and intra-layer capacitances which depend on not so well controlled parameters such as insulation thickness (difficult to control), how perfectly parallel the windings are, etc. Consequently, two probes with $L_{pA} \approx L_{pB}$, $R_{pA} \approx R_{pB}$, and $C_{pA} \approx C_{pB}$ with $L_{pA}C_{pA}=L_{pB}C_{pB}$ and $R_{pA}C_{pA}=R_{pB}C_{pB}$ will not necessarily have the same response of detection characteristics especially when attempting to distinguish between cancer and normal tissue.

Accordingly, the present invention recognizes that if two probes have $L_{pA}C_{pA}=L_{pB}C_{pB}$ and $R_{pA}C_{pA}=R_{pB}C_{pB}$ and their responses are different in being able to distinguish cancer from normal tissue, their responses can be made identical by adding the appropriate miniscule capacitance in the external circuit with no regard to the criterion $L_{pA}C_{pA}=L_{pB}C_{pB}$ and $R_{pA}C_{pA}=R_{pB}C_{pB}$. This allows the improvement of the sensitivity of a particular (already fabricated) probe.

Figure 34:
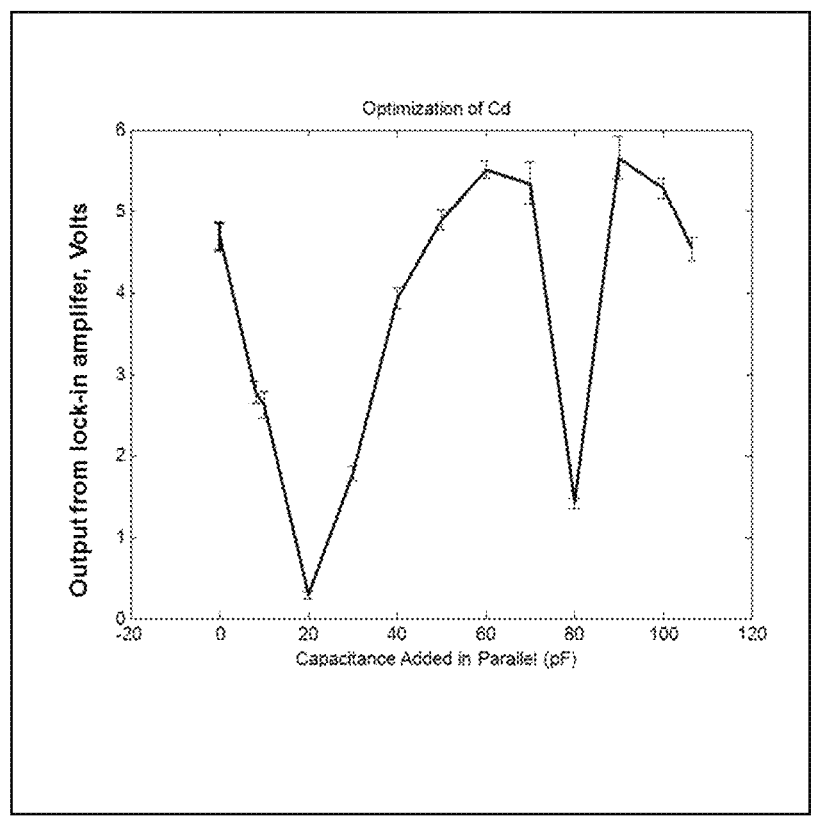

The present invention recognizes that it is important to have enough peaks so as to have the last peak run into the first peak of the next duty cycle. In other words, it is not the number of peaks that determines the sensitivity of the electromagnetic probe to different tissue types but the fact that a peak from the ringing must run into the first peak of the next duty cycle (see FIG. 29). Moreover, it is how this last peak runs into the first peak of the next duty cycle that determines the sensitivity of the probe in distinguishing different tissue types. If the intersection between the last peak and the first peak of the next duty cycle happens on the sloping sides of the first peak of the next duty cycle, then the probe is more sensitive compared to when the intersection happens on the peak or valley of the last peak. This is shown in FIGS. 30-33, and summarized in FIG. 34. In one embodiment of the invention, the intersection of the rising side (or falling side) of the last peak of the duty cycle will intersect the rising side of the first peak of the next duty cycle. In another embodiment, the intersection of the rising side (or falling side) of the last peak will intersect the falling side of the first peak of the next duty cycle. In other words, in the preferred embodiment, the rising or falling side of the last peak of the duty cycle will intersect a sloping side of the first peak of the next duty cycle.

Figure 35:
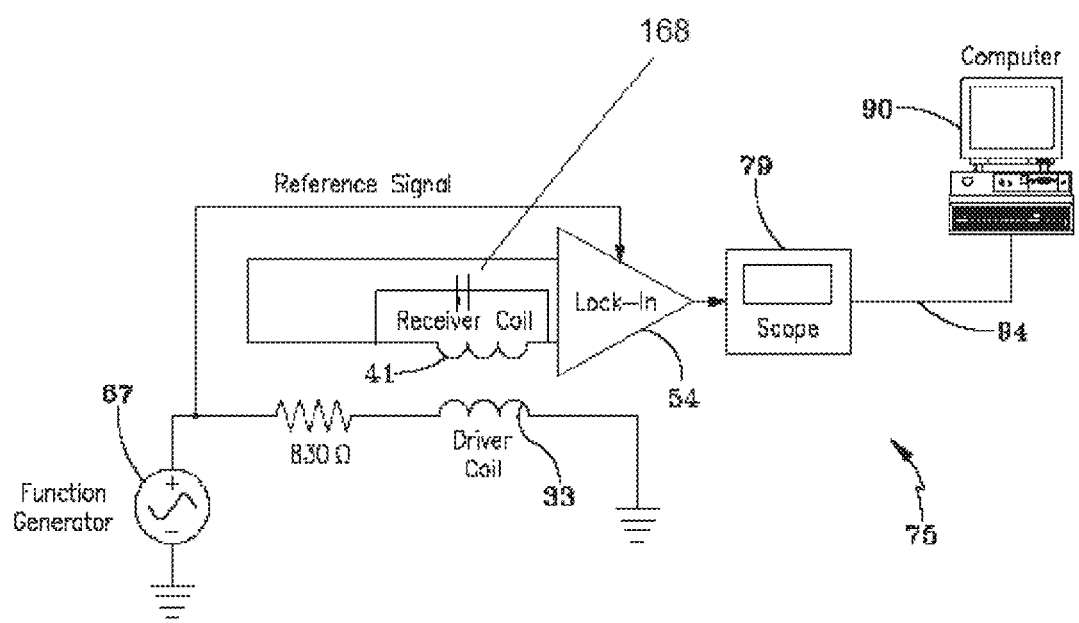
FIG. 35 illustrates one example embodiment of the present invention with a capacitor added in parallel with the receiver coil.

Accordingly, in one embodiment the coil is designed so the last peak coincides on the sloping sides of the of the first peak of the next cycle. There are two ways to accomplish this: (1) the inductances and capacitances of the primary and detector coils can be changed by (a) changing the number of turns in the coil, and/or (b) changing the insulation thickness or material of the wire used, and/or (2) by adding small (on the order of tens of picofarads) capacitance in the external circuit of the detector coil to optimize the output signal from the lock-in amplifier for a given coil design. For example, FIG. 35 illustrates one embodiment of the present invention where a small capacitance 168 is added in parallel to the receiver coil.

What is claimed is:

1. A system for detecting differences in tissue property in a tissue of an animal or human, comprising:
   a probe shaped in a configuration so that it may be hand-held comprising a driver coil and a receiver coil;
   an alternating current or power supply connected to the driver coil configured to provide a non-sinusoidal, asymmetric signal to the driver coil with a frequency between 1 Hz and 1 MHz for inducing eddy currents in the tissue when the probe is placed adjacent to the tissue;
   a measurement circuit, operably connected to the receiver coil and configured to measure a phase shift between the voltage or current on the driver coil and the voltage or current produced thereby in the receiver coil when the driver and receiver coils are positioned adjacent to the tissue, wherein the voltage or current produced in the receiver coil has at least a first and second duty cycle each comprised of multiple peaks and wherein the driver coil and receiver coil has inductances and capacitances so the last peak of the voltage or current produced in the first duty cycle coincides on a sloping side of the first peak of the second duty cycle; and
   a hardware processor operably connected to the measurement circuit, the hardware processor programmed with one or more software routines executing on the hardware processor to compare the phase shift between the voltage or current on the driver coil and the voltage or current in the receiver coil to detect differences in tissue property.

2. A system according to claim 1 wherein the measurement circuit is a lock-in amplifier configured to provide a DC output voltage indicative of the detected phase shift between the voltage or current on the driver coil and the voltage or current produced thereby in the receiver coil.

3. A system according to claim 1, further comprising:
a means for raster scanning the probe at various positions across the tissue; and
wherein the measurement circuit provides the measured phase shift between the input voltage or current imposed on the driver coil and the alternating voltage or current induced in the receiver coil at positions across the tissue in order to create an image.

4. A system according to claim 1, wherein the measurement circuit is configured to measure a change in amplitude between the voltage or current on the driver coil and the voltage or current produced thereby in the receiver coil, and
wherein the hardware processor is programmed with one or more software routines executing on the hardware processor to compare differences in amplitude between the voltage or current on the driver coil and the voltage or current produced thereby in the receiver coil to detect the differences in tissue property.

5. A system according to claim 1, wherein the probe diameter is 13.3 mm.

6. A system according to claim 1, wherein the alternating current or power supply connected to the driver coil is configured to provide a sawtooth signal to the driver coil; and wherein the system is further comprised of a capacitor added in parallel to the receiver coil.

7. A method for detecting differences in tissue property in a tissue of an animal or human, comprising the steps of:
placing a probe adjacent to the tissue, the probe shaped in a configuration so that it may be hand-held comprising a driver coil and a receiver coil;
connecting an alternating current or power supply to the driver coil;
providing a non-sinusoidal, asymmetric signal to the driver coil with a frequency of between 1 Hz and 1 MHz for inducing eddy currents in the tissue when the probe is placed adjacent to the tissue;
connecting a measurement circuit to the receiver coil;
measuring a phase shift between the voltage or current on the driver coil and the voltage or current produced thereby in the receiver coil when the driver and receiver coils are positioned adjacent to the tissue, wherein the voltage or current produced in the receiver coil has at least a first and second duty cycle each comprised of multiple peaks;
introducing inductances and capacitances in the driver coil and receiver coil so the last peak of the voltage or current produced in the first duty cycle coincides on a sloping side of the first peak of the second duty cycle; and
processing the measured phase shift data to detect differences in tissue property.

8. A method according to claim 7, further comprising the steps of: measuring a change in amplitude between the voltage or current on the driver coil and the voltage or current produced thereby in the receiver coil, and
comparing differences in amplitude between the voltage or current on the driver coil and the voltage or current produced thereby in the receiver coil to detect the differences in tissue property.

9. A system for detecting differences in tissue property identifying in a tissue of an animal or human, comprising:
a probe shaped in a configuration so that it may be hand-held comprising a driver coil and a receiver coil;
an alternating current or power supply connected to the driver coil configured to provide a non-sinusoidal, asymmetric signal to the driver coil with a frequency of between 1 Hz and 1 MHz for inducing eddy currents in the tissue when the probe is placed adjacent to the tissue;
a measurement circuit, operably connected to the receiver coil and configured to measure a phase shift between the voltage or current on the driver coil and the voltage or current produced thereby in the receiver coil when the driver and receiver coils are positioned adjacent to the tissue, wherein the voltage or current produced in the receiver coil has at least a first and second duty cycle each comprised of multiple peaks; and
a hardware processor operably connected to the measurement circuit, the hardware processor programmed with one or more software routines executing on the hardware processor to compare the phase shift between the voltage or current on the driver coil and the voltage or current produced thereby in the receiver coil to detect differences in tissue property; and
a capacitor added in parallel to the receiver coil so the last peak of the voltage or current produced in the first duty cycle coincides on a sloping side of the first peak of the second duty cycle.

10. A system according to claim 9, wherein the measurement circuit is a lock-in amplifier configured to provide a DC output voltage indicative of the detected phase shift between the voltage or current on the driver coil and the voltage or current produced thereby in the receiver coil.

11. A system according to claim 9, further comprising:
a means for raster scanning the probe at various positions across the tissue; and
wherein the measurement circuit is adapted to provide the measured phase shift between the input voltage or current imposed on the driver coil and the alternating voltage or current induced in the receiver coil at positions across the tissue in order to create an image.

12. A system according to claim 9, wherein the measurement circuit is configured to measure a change in amplitude between the voltage or current on the driver coil and the voltage or current produced thereby in the receiver coil, and
wherein the hardware processor is programmed with one or more software routines executing on the hardware processor to compare the differences in amplitude between the voltage or current on the driver coil and the voltage or current produced thereby in the receiver coil to detect the differences in tissue property.

13. A system according to claim 9, wherein the probe diameter is 13.3 mm.

14. A system according to claim 9, wherein the capacitor in parallel with the receiver coil is a small capacitor in the order of tens of picofarads.

* * * * *